United States Patent
Kuwabara et al.

(10) Patent No.: US 9,351,699 B2
(45) Date of Patent: May 31, 2016

(54) RADIOGRAPHY SYSTEM AND RADIATION SOURCE CONTROLLER

(75) Inventors: Takeshi Kuwabara, Ashigarakami-gun (JP); Takeshi Kamiya, Ashigarakami-gun (JP); Yusuke Kitagawa, Ashigarakami-gun (JP); Takashi Tajima, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 482 days.

(21) Appl. No.: 13/561,919

(22) Filed: Jul. 30, 2012

(65) Prior Publication Data

US 2013/0058453 A1 Mar. 7, 2013

(30) Foreign Application Priority Data

Sep. 5, 2011 (JP) .................................. 2011-193192

(51) Int. Cl.
*H05G 1/44* (2006.01)
*G01N 23/04* (2006.01)
(Continued)

(52) U.S. Cl.
CPC *A61B 6/542* (2013.01); *H04N 5/32* (2013.01); *H04N 5/2351* (2013.01); *H05G 1/44* (2013.01)

(58) Field of Classification Search
CPC ........ A61B 6/542; A61B 6/4233; A61B 6/00; A61B 6/4283; A61B 6/547; A61B 6/548; A61B 6/4266; A61B 6/4405; A61B 6/545; A61B 6/56; A61B 2560/0271; H05G 1/60; G03B 42/02; G06T 7/00; Y10S 378/901
USPC ................. 378/97, 62, 108, 205; 250/370.08, 250/370.09; 382/132
See application file for complete search history.

(56) References Cited

U.S. PATENT DOCUMENTS 4,097,741 A * 6/1978 Pfeiler et al. ..................... 378/97
4,454,606 A * 6/1984 Relihan ............................ 378/97
(Continued)

FOREIGN PATENT DOCUMENTS

EP 1 001 665 A2 5/2000
EP 1 179 741 A2 2/2002
(Continued)

OTHER PUBLICATIONS

Communication pursuant to Article 94(3) EPC, dated Jun. 3, 2013, issued in corresponding EP Application No. 12177222.2, 6 pages.
(Continued)

*Primary Examiner* — Michael Logie
(74) *Attorney, Agent, or Firm* — Sughrue Mion, PLLC

(57) ABSTRACT

A source controller unit for controlling an x-ray source is provided with a detection signal interface for receiving detection signals from detective pixels of an electronic cassette or an integrated value of the detection signals only, or an interface for receiving a radiation stopping signal only. The source controller unit receives other radiation signals than the radiation stopping signal, such as a radiation admitting signal, through a radiation signal interface. The source controller unit uses the detection signals, the integrated value thereof, or the radiation stopping signal as exposure control signals for stopping radiation from the x-ray source. Since the exposure control signals are received on the specific interface therefor, the source controller unit does not need signal sorting operation nor receive different kinds of signals at the same time, improving the speed of radiation stopping procedure.

18 Claims, 20 Drawing Sheets

(51) Int. Cl.
*A61B 6/00* (2006.01)
*H04N 5/32* (2006.01)
*H04N 5/235* (2006.01)

(56) References Cited

U.S. PATENT DOCUMENTS

| | | | | |
|---|---|---|---|---|
| 6,151,383 | A * | 11/2000 | Xue et al. | 378/108 |
| 6,208,710 | B1 * | 3/2001 | Nagai | A61B 6/00 378/108 |
| 6,448,561 | B1 * | 9/2002 | Kaifu | 250/370.09 |
| 7,079,189 | B2 * | 7/2006 | Tsujii | G01T 1/2928 250/208.4 |
| 8,824,634 | B2 * | 9/2014 | Lalena | A61B 6/08 378/108 |
| 8,867,705 | B2 * | 10/2014 | Lalena | A61B 6/08 378/166 |
| 2002/0186813 | A1 * | 12/2002 | Tamura | H04N 5/321 378/98.8 |
| 2004/0096035 | A1 * | 5/2004 | Yamazaki | A61B 6/107 378/97 |
| 2004/0223587 | A1 * | 11/2004 | Tsujii | 378/97 |
| 2004/0234032 | A1 * | 11/2004 | Nokita | 378/98.8 |
| 2005/0211907 | A1 * | 9/2005 | Wendt et al. | 250/370.07 |
| 2009/0084962 | A1 * | 4/2009 | Kito | G01T 7/00 250/369 |
| 2009/0087073 | A1 * | 4/2009 | Kito | A61B 6/00 382/132 |
| 2009/0189761 | A1 * | 7/2009 | Nishino et al. | 340/540 |
| 2009/0220048 | A1 * | 9/2009 | Ohta | A61B 6/4233 378/98 |
| 2010/0002831 | A1 * | 1/2010 | Maack | 378/16 |
| 2010/0054419 | A1 * | 3/2010 | Watanabe | 378/117 |
| 2010/0061507 | A1 * | 3/2010 | Fujii | 378/28 |
| 2010/0320392 | A1 * | 12/2010 | Nishino | A61B 6/4233 250/370.08 |
| 2011/0164723 | A1 * | 7/2011 | Park et al. | 378/62 |
| 2011/0180717 | A1 * | 7/2011 | Okada | 250/370.08 |
| 2011/0249791 | A1 * | 10/2011 | Wang | A61B 6/08 378/62 |
| 2011/0249792 | A1 * | 10/2011 | Lalena et al. | 378/62 |
| 2011/0249799 | A1 * | 10/2011 | Lalena et al. | 378/97 |
| 2012/0132821 | A1 * | 5/2012 | Kuwabara | 250/370.08 |
| 2013/0058454 | A1 * | 3/2013 | Kuwabara et al. | 378/62 |
| 2013/0126742 | A1 * | 5/2013 | Hayun et al. | 250/366 |
| 2013/0148782 | A1 * | 6/2013 | Tajima | 378/62 |
| 2014/0177798 | A1 * | 6/2014 | Kitagawa et al. | 378/62 |
| 2014/0211922 | A1 * | 7/2014 | Kuwabara et al. | 378/97 |

FOREIGN PATENT DOCUMENTS

| | | | |
|---|---|---|---|
| EP | 1 440 660 A2 | 7/2004 | |
| JP | 2003-302716 A | 10/2003 | |
| JP | 2003302716 A | 10/2003 | |
| JP | 2006333898 A * | 12/2006 | A61B 6/00 |
| WO | 01/76228 A1 | 10/2001 | |
| WO | 2005/098535 A1 | 10/2005 | |
| WO | 2006/046206 A1 | 5/2006 | |

OTHER PUBLICATIONS

Communication, dated Oct. 19, 2012, issued in corresponding EP Application No. 12177222.2, 10 pages.
Notification of Reasons for Refusal, dated Jul. 30, 2014, issued in corresponding JP Application No. 2011-193192, 9 pages in English and Japanese.
The First Office Action, dated Aug. 11, 2015, issued in corresponding CN Application No. 201210268680.6, 20 pages in English and Chinese.
The Second Office Action, dated Mar. 16, 2016, issued in corresponding CN Application No. 201210268680.6, 22 pages in English and Chinese.

* cited by examiner

FIG.6

| No. | TARGET SITE | TUBE VOLTAGE (kV) | S VALUE | ... |
|---|---|---|---|---|
| 1 | CHEST PA | 120 | S1 | |
| 2 | CHEST AP | | S2 | |
| 3 | CHEST LATERAL | | S3 | |
| ⋮ | ⋮ | | ⋮ | ... |
| 48 | HEAD PA | 50 | S48 | |
| 49 | HEAD AP | | S49 | |
| 50 | HEAD LATERAL | | S50 | |
| ⋮ | ⋮ | | ⋮ | |

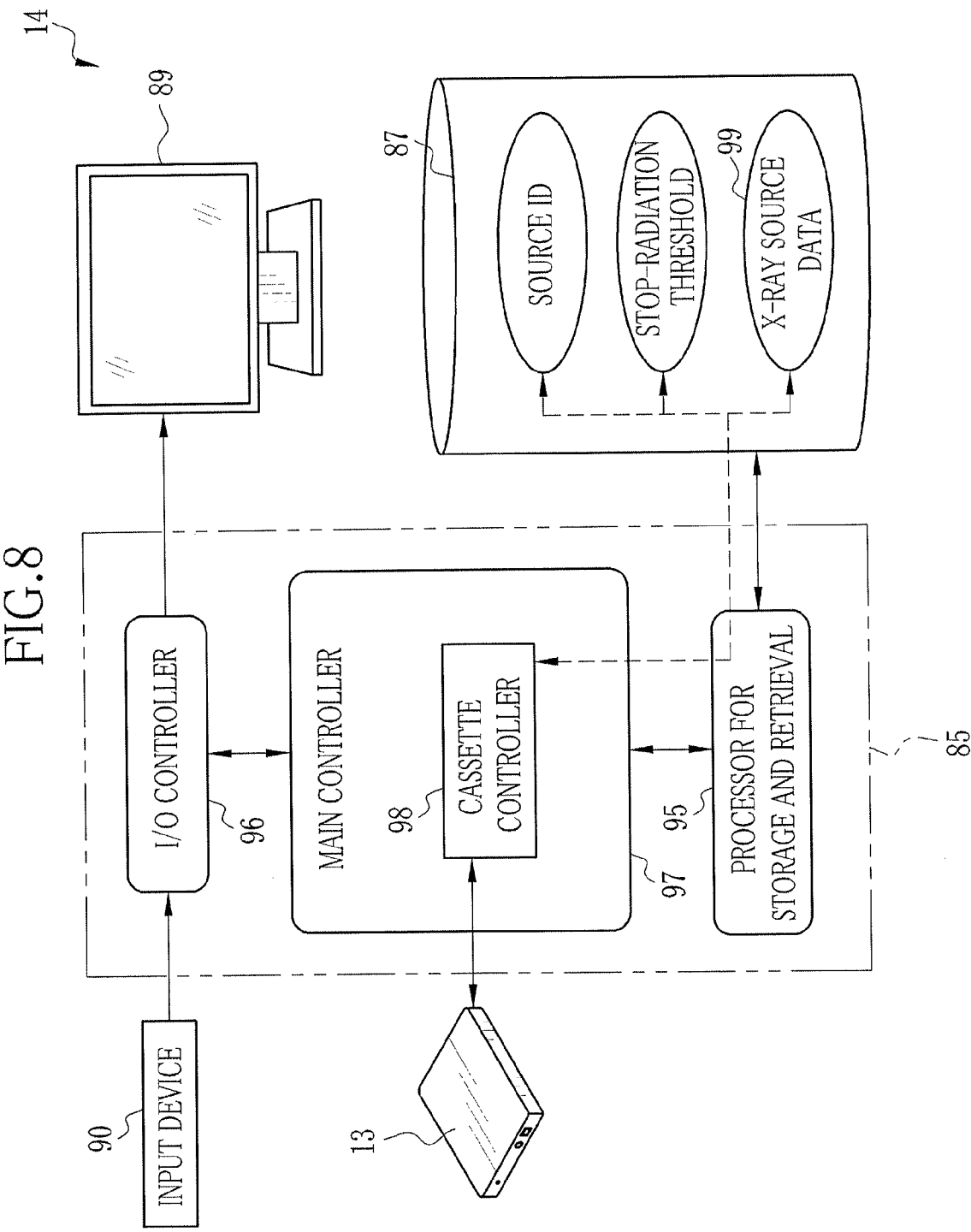

FIG.9

| SOURCE ID | REGIONAL TYPE | | ACQUISITION SETTING | AEC SPECIFICATION | | CORRECTION DATA |
| --- | --- | --- | --- | --- | --- | --- |
| | REGION | TYPE | | INTEGRATOR CKT | LOCATION OF X-RAY DETECTION FIELD | |
| 0001 | DOMESTIC (JP) 1 | NON-INSTALLATION-PRIORITY | No.1 120kV 1mAs X-RAY DETECTION FIELD Fa, Fb··· ··· | ABSENT | Fa:(x1,y1) ~(x2,y2) ··· ⋮ | (graph: NEW AEC DETECTION SIGNAL vs EX-AEC DETECTION SIGNAL; TUBE VOLTAGE A, B, C, D) |
| | DOMESTIC (JP) 2 | NON-INSTALLATION-PRIORITY | | | | |
| | US 1 | INSTALLATION-PRIORITY | | | | |
| | US 2 | NON-INSTALLATION-PRIORITY | | | | |
| | EP 1 | INSTALLATION-PRIORITY | | | | |
| | EP 2 | INSTALLATION-PRIORITY | | | | |
| | ASIA 1 | INSTALLATION-PRIORITY | | | | |
| | ASIA 2 | INSTALLATION-PRIORITY | | | | |
| 0002 | DOMESTIC (JP) 1 | NON-INSTALLATION-PRIORITY | No.1 115kV 1.5mAs X-RAY DETECTION FIELD Fa~Fe··· ··· | PRESENT | Fa:(x3,y3) ~(x4,y4) ··· ⋮ | (graph: NEW AEC DETECTION SIGNAL vs EX-AEC DETECTION SIGNAL; TUBE VOLTAGE A, B, C, D) |
| | DOMESTIC (JP) 2 | NON-INSTALLATION-PRIORITY | | | | |
| | US 1 | INSTALLATION-PRIORITY | | | | |
| | US 2 | INSTALLATION-PRIORITY | | | | |
| | EP 1 | INSTALLATION-PRIORITY | | | | |
| | EP 2 | INSTALLATION-PRIORITY | | | | |
| | ASIA 1 | INSTALLATION-PRIORITY | | | | |
| | ASIA 2 | INSTALLATION-PRIORITY | | | | |

| REGIONAL TYPE | INSTALLATION-PRIORITY | NON-INSTALLATION-PRIORITY |
|---|---|---|
| INSTALLATION CONVENIENCE | ○ | △ |
| IMAGE QUALITY | △ | ○ |
| OUTPUT ADDRESS | DETECTION SIGNAL I/F | RADIATION SIGNAL I/F |
| OUTPUT FORMAT | DETECTION SIGNAL | RADIATION STOPPING SIGNAL |
| CORRECTION OF DETECTED VALUE | NECESSARY | NECESSARY |
| REPLACEMENT OF THRESHOLD | UNNECESSARY | NECESSARY |
| DECISION TO STOP RADIATION | MADE ON X-RAY SOURCE SIDE | MADE ON CASSETTE SIDE |

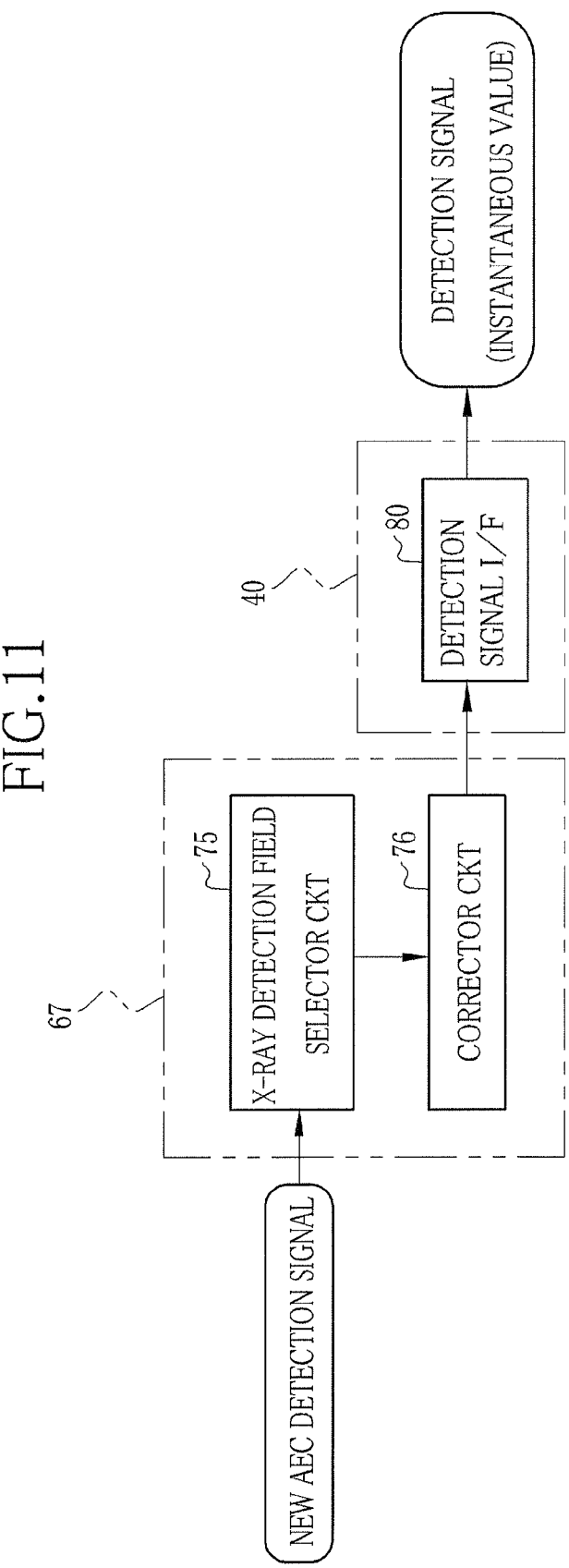

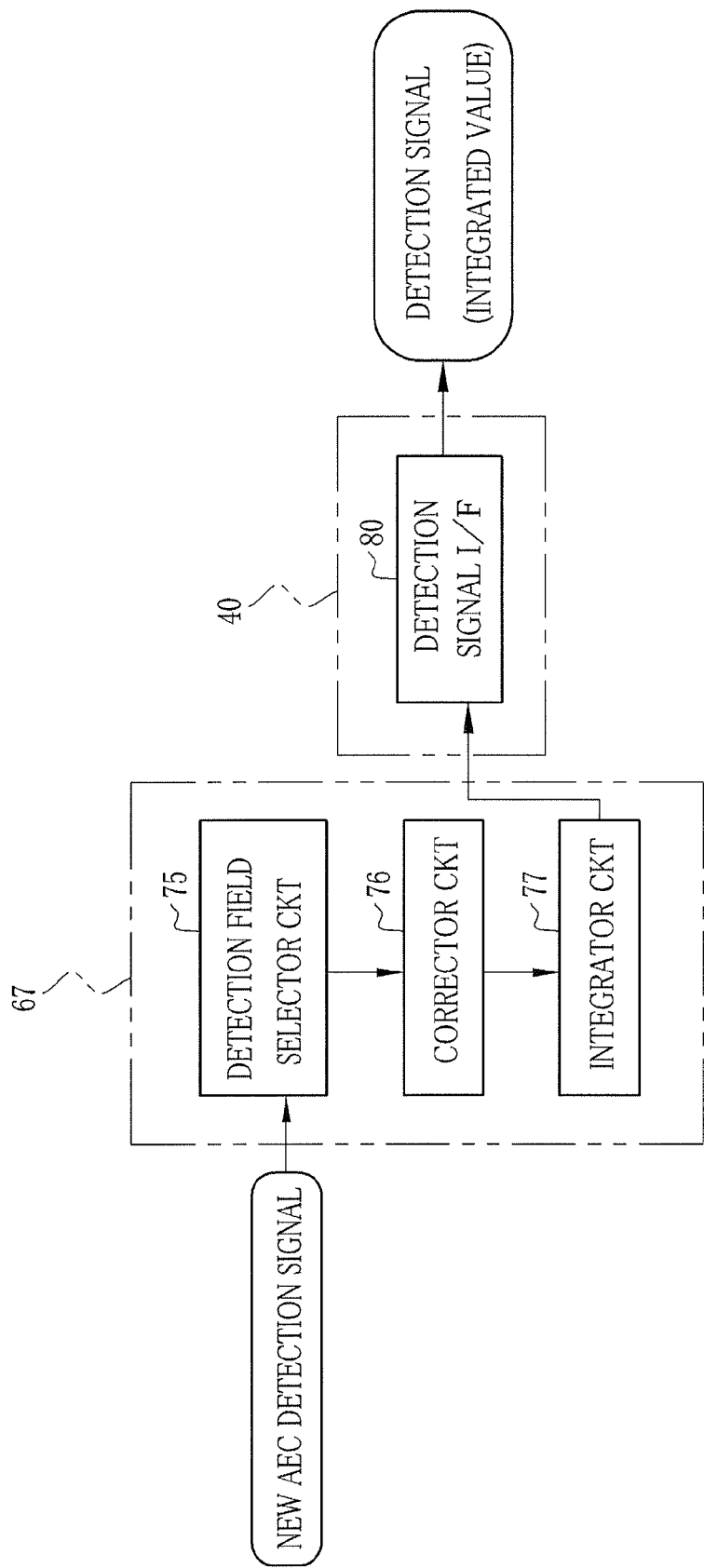

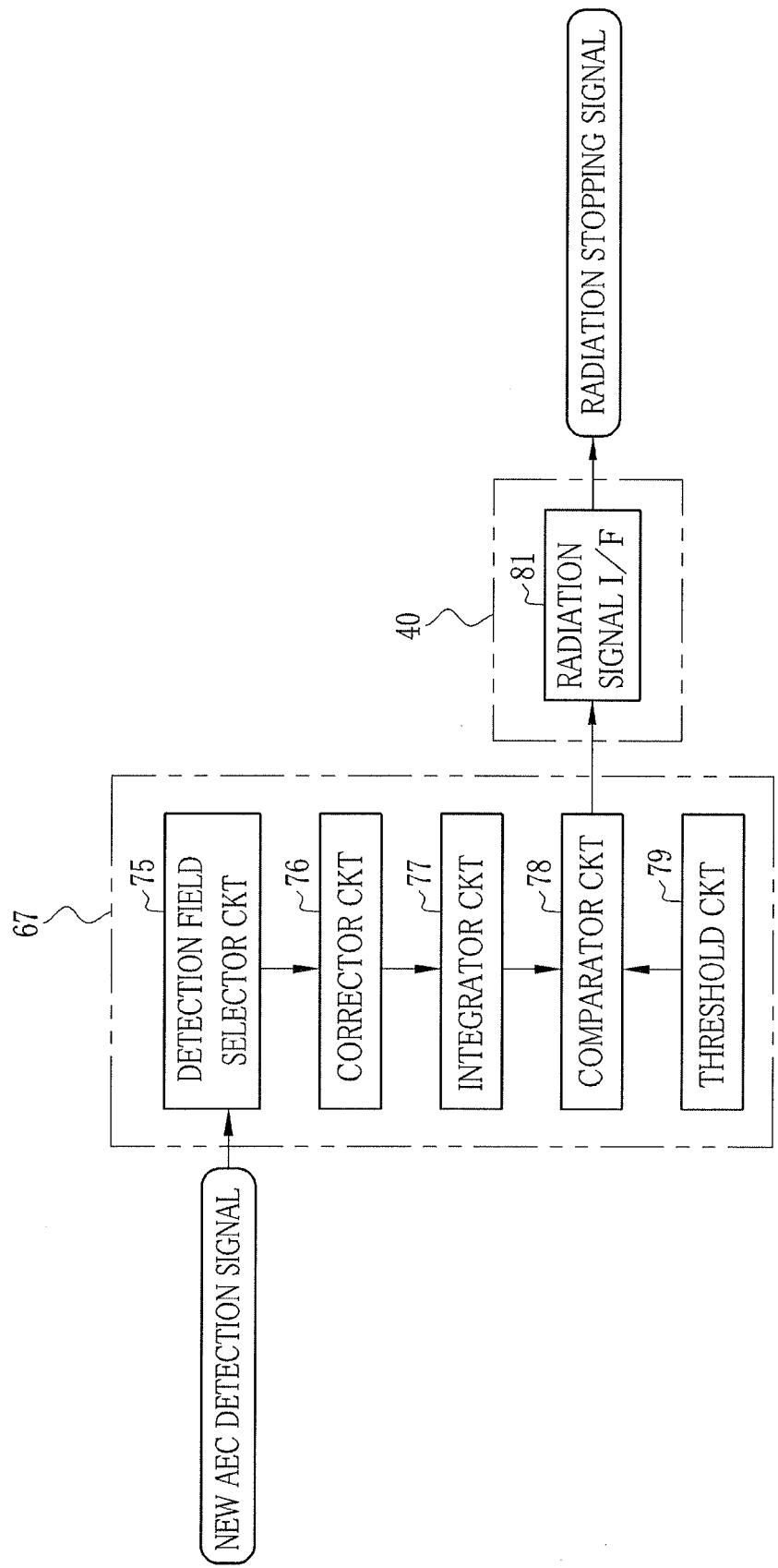

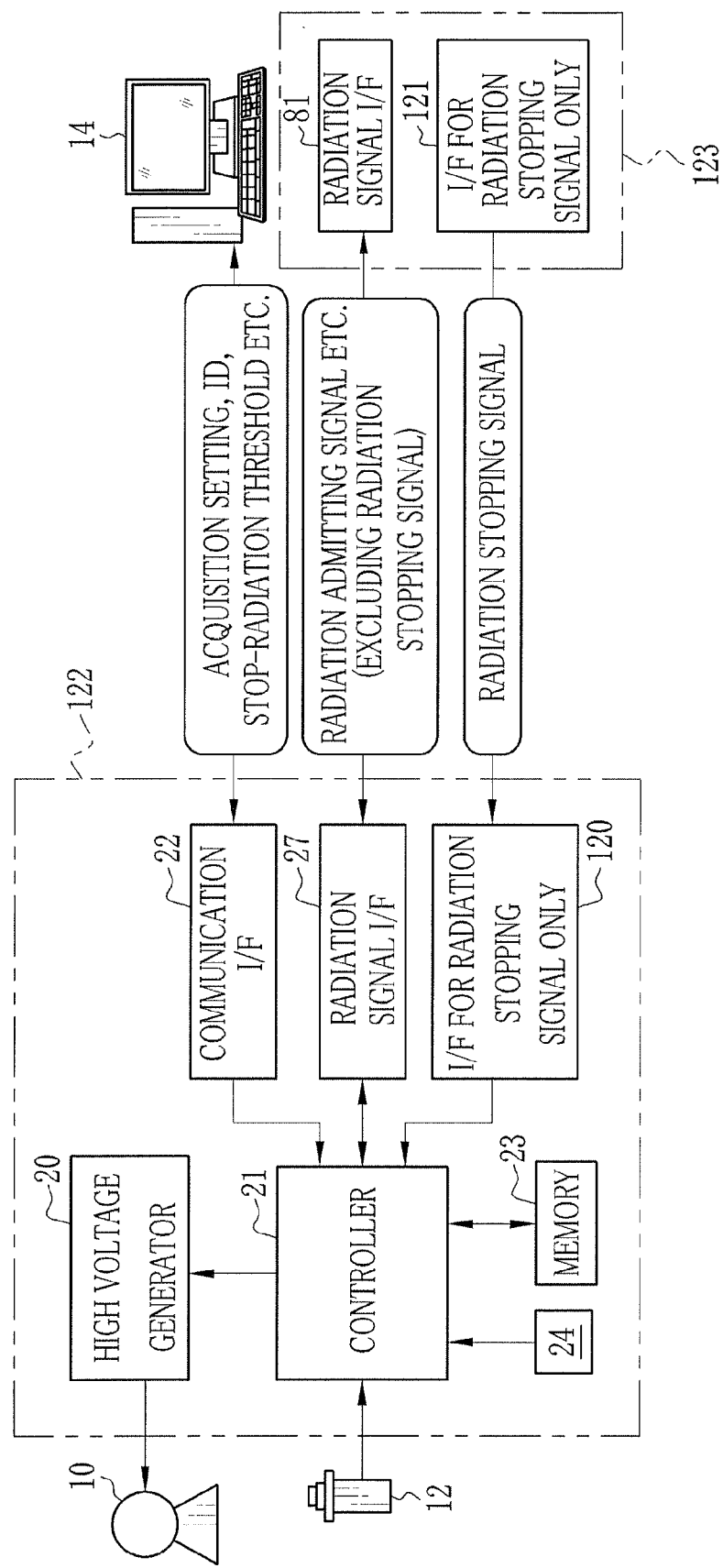

RADIOGRAPHY SYSTEM AND RADIATION SOURCE CONTROLLER

BACKGROUND OF THE INVENTION

1. Field of the Invention

The present invention relates to a radiography system consisting of a radiation projector for projecting radioactive rays toward a subject and a radiographic imaging device for acquiring an image of the subject from the radioactive rays that are incident on the imaging device after penetrating the subject. The present invention relates also to a source controller for controlling a radiation source included in the radiation projector.

2. Description of the Related Art

In the medical field, radiography systems utilizing radioactive rays, such as x-rays, for imaging are widely known. An x-ray radiography system, an example of radiography systems, includes an x-ray projector for projecting x-rays toward a subject and an x-ray imaging apparatus for acquiring a radiograph or x-ray image of the subject from the x-rays that have penetrated the subject. The x-ray projector includes an x-ray source, a source controller unit, and an activation switch for inputting an x-ray radiation starting signal. The x-ray imaging apparatus includes an x-ray image detector for detecting an x-ray image or x-ray images from incident x-rays, and a console for controlling operation of the x-ray image detector and processing the x-ray images for various image-renderings.

In the field of x-ray radiography system, x-ray image detectors using a flat panel detector (FPD) in place of conventional x-ray film or imaging plates (IP) have recently been widely spread. The FPD has a large number of pixels arranged in a matrix to accumulate signal charges corresponding to x-rays incident on the respective pixels. The FPD converts the accumulated signal charges to a voltage signal through a signal processing circuit, to detect an x-ray image representative of graphic information on the subject, and output the detected x-ray image as digital image data.

Portable x-ray image detectors, called electronic cassettes, have also been used in practice, each of which contains a flat panel detector in a rectangular box-shaped body. The plane size of the electronic cassette is about the same as those of radiographic film cassettes and IP cassettes, so that the electronic cassette can be removably mounted in a conventional radiographic stand or table which is adapted to the film cassette or IP cassette. In addition, the electronic cassette can be used independently. For example, in order to image such a site of a test subject that is hard to image using a stationary image detector that is fixedly mounted in the stationary radiographic stand or table, the portable electronic cassette may be put on a bed with the test subject or may be held directly by the test subject. Moreover, the electronic cassette may be carried around for use in home medical care or emergency medical care at accident sites or disaster sites outside the hospital.

In the FPD type image detector, charge-resetting operation for clearing the accumulated charges off the pixels is periodically carried out before starting charge accumulating operation, in order to reduce the influence of noises to the minimum. Accordingly, it is generally necessary for the radiography system using the FPD to synchronize the timing of x-ray radiation with the end of charge-resetting operation and the start of charge accumulating operation. For this purpose, in an example, a wired interface is interconnected between the source controller unit and the x-ray image detector (electronic cassette) so that the source controller unit sends a signal as a cue to the electronic cassette at the start of x-ray radiation, upon which the electronic cassette proceeds to the accumulating operation.

As an automatic exposure control (AEC) system, a conventional x-ray radiography system is provided with a sensor, such as an ion chamber, separately from the electronic cassette. The sensor measures x-ray dose applied to the test subject, in order to stop x-ray radiation from the x-ray source when the integrated amount of x-ray dose gets to a predetermined threshold level.

There have also been suggested such AEC systems as disclosed in JPA 2003-302716, wherein a photo timer or AEC sensor is integrated into an FPD type electronic cassette instead of a separate sensor like an ion chamber. An output terminal of the photo timer is connected to an interruption signal input terminal of a radiographic stand or table, through which the photo timer is connected to an x-ray projector. An output signal from the photo timer may be an x-ray interruption signal (radiation stopping signal) or an analog signal (detection signal or voltage level). In the former case, electric charges from the photo timer are integrated inside the electronic cassette, and the integrated value is compared with a threshold level, so that the x-ray interruption signal will be output when the integrated value gets over the threshold level. In the latter case, the analog signal from the photo timer is integrated after being received on the x-ray projector and the integrated value is compared with the threshold level to decide the time to stop x-ray radiation.

Because a delay in radiation stopping procedure by the source controller will lower the quality of acquired x-ray image and overexpose the patient as a test subject to x-rays, the radiation stopping procedure should be done in no time. For instance, requisite exposure time for radiography of chest is 50 ms or so. Within such a short time, the radiography system must deactivate the x-ray source as soon as it is confirmed by the detection signal from the AEC sensor of the electronic cassette that the radiation dose reaches a sufficient amount. However, in a case where the source controller and the x-ray image detector using the FPD are connected to each other through a wired interface, the single interface must manage to exchange not only AEC signals for automatic exposure control, like the x-ray interruption signal as mentioned in the above prior art, but also a variety of other signals, such as a radiation starting signal, data of image acquisition settings. In that case, the signals are more likely to interfere with each other, hindering exact transmission of the AEC signals and increasing the risk of delay in the radiation stopping procedure.

As a solution for the above problem, it may be possible to control signal transmissions such that the x-ray image detector will not send other signals than those used for automatic exposure control while the AEC signals for automatic exposure control are exchanged between the source controller and the x-ray image detector. However, this solution will require complicated control of the signal transmissions.

Besides the above problem, another problem occurs when an electronic cassette with an AEC sensor attached should be used in combination with an already installed x-ray projector, which has its own AEC sensor, e.g. a conventional ion chamber. In that case, it is necessary to connect the AEC sensor of the electronic cassette to a source controller of the existing x-ray projector. In many cases, however, x-ray projectors and x-ray imaging apparatuses are manufactured by different markers from each other. When an x-ray projector and an x-ray imaging apparatus of different markers constitute a radiography system, it is hard to specify how the signals exchanged between these machines would be processed inside the respective machines. For this reason, it has been difficult to assure the quality of such an x-ray radiography system that consists of an x-ray projector and an electronic cassette of a different marker from the x-ray projector, and an AEC sensor of the electronic cassette is connected to a source controller of the x-ray projector. Even while the respective markers guarantee the individual machines, if these machines are combined into a radiography system, any of these machines may operate unexpectedly. Consequently, it has been difficult to guarantee that the radiography system consisting of machines of different markers will satisfy the requirement for the above-mentioned extremely high-speed processing to terminate the radiation.

The above prior art does not disclose any solution for ensuring precise and high-speed procedures for stopping radiation in time.

SUMMARY OF THE INVENTION

In view of the foregoing, an object of the present invention is to provide a radiography system and a source controller unit, whereby the source controller unit can accomplish the radiation stopping procedures stably without delay.

In a radiography system including a radiation source for projecting radioactive rays toward a subject, a source controller unit for controlling activation of the radiation source, and a radiographic image detector for detecting a radiograph of the subject from radioactive rays penetrating the subject and being incident on an imaging plane of a detection panel, the present invention provides the source controller unit with a first signal interface for receiving exposure control signals only, and a second signal interface for receiving other signals than the exposure control signals, on the assumption that the radiographic image detector has a sensor for detecting the incident amount of radioactive rays and outputs exposure control signals to the source controller unit in order to stop radiation from the radiation source when a cumulative amount of the incident radioactive rays reaches a predetermined threshold.

The exposure control signals may include detection signals from the sensor an integrated value of the detection signals, or a radiation stopping signal that is generated based on the integrated value of the detection signals.

Preferably, the radiographic image detector comprises a third signal interface for sending the exposure control signals only and a fourth signal interface for sending other signals.

Preferably, the fourth signal interface wirelessly transmits the other signals than the exposure control signals to the second signal interface.

Preferably, the radiographic image detector includes a detection field selecting device for selecting a detection field of the sensor in accordance with a detection field of an ex-sensor which the source controller unit has previously used for automatic exposure control, on the basis of location data of the detection field of the ex-sensor when the sensor provided in the radiographic image detector is used in place of the ex-sensor.

The detection field selecting device preferably takes the posture of the radiographic image detector into consideration on selecting the detection field.

Preferably, the radiographic image detector includes a correcting device for correcting detection signals from the sensor to be equivalent to detection signals from an ex-sensor which has been used by the source controller unit for automatic exposure control, when the sensor provided in the radiographic image detector is used in place of the ex-sensor in order to exclude influence of variations in intervening parts between the radiation source and the imaging plane of the detection panel of the radiographic image detector from the detection signals.

The intervening parts may include at least one of a housing that covers the detection panel of the radiographic image detector a scintillator for converting radioactive rays into visible light, and a grid for eliminating diffused radioactive rays as diffused through the subject.

Preferably, data of correlation between detection signals from the sensor and detection signals from the ex-sensor is stored in a storage device and the correcting device corrects detection signals from the sensor on the basis of the correlation data.

Preferably, the radiographic image detector comprises an integrating device for integrating the detection signals corrected through the correcting device.

The radiographic image detector may send out the detection signals of the sensor as the exposure control signal when the source controller unit has a function of integrating the detection signals. The radiographic image detector sends out the integrated value of the detection signals as the exposure control signal when the source controller unit has no function of integrating the detection signals.

Preferably, the radiographic image detector includes a comparing device that compares the integrated value of the detection signals from the integrating device with a given threshold level and outputs a radiation stopping signal when the integrated value reaches the given threshold level.

Preferably, the source controller unit transmits through the second signal interface an inquiry signal to the radiographic image detector inquiring whether the radiation source may start the radiation, and receives a radiation admitting signal from the radiographic image detector through the second signal interface.

According to another aspect of the present invention, a source controller unit for controlling activation of a radiation source comprises a first signal interface for receiving only exposure control signals output from a sensor which detects the amount of radioactive rays having been projected toward and penetrated through a subject, the exposure control signal being used for stopping radiation from the radiation source when an integrated amount of the radioactive rays reaches a predetermined threshold; and a second signal interface for receiving other signals than the exposure control signals.

According to the present invention, the source controller unit receives the exposure control signals, such as the detection signals from the sensor of the radiographic image detector or the radiation stopping signal, through the specific interface therefor. Consequently, the source controller unit does not need any sorting operation nor receive different kinds of signals at the same time. Thus, stability and speed of radiation stopping procedure is improved.

BRIEF DESCRIPTION OF THE DRAWINGS

The above and other objects and advantages of the present invention will be more apparent from the following detailed description of the preferred embodiments when read in connection with the accompanied drawings, wherein like reference numerals designate like or corresponding parts throughout the several views, and wherein:

FIG. 6 is a table diagram showing image acquisition settings entered on a console of the radiography system;

FIG. 8 is a block diagram illustrating functions of the console and data streams in the system;

FIG. 9 is a table diagram showing source data on various kinds of radiation sources;

FIG. 10 is a table diagram showing differences between two regional types of the system;

FIG. 11 is a diagram illustrating how the AEC section and the communicator section work when the regional type is of installation-priority type and the source controller unit includes an integrator circuit;

FIG. 12 is a diagram illustrating how the AEC section and the communicator section work when the regional type is of installation-priority type and the source controller unit includes no integrator circuit;

FIG. 13 is a diagram illustrating how the AEC section and the communicator section work when the regional type is of non-installation-priority type;

FIG. 19 is a block diagram illustrating an embodiment wherein radiation signals other than radiation stopping signal are exchanged through radiation signal interfaces, while the radiation stopping signal is transmitted through detection signal interfaces.

DESCRIPTION OF THE PREFERRED EMBODIMENTS

Figure 1:
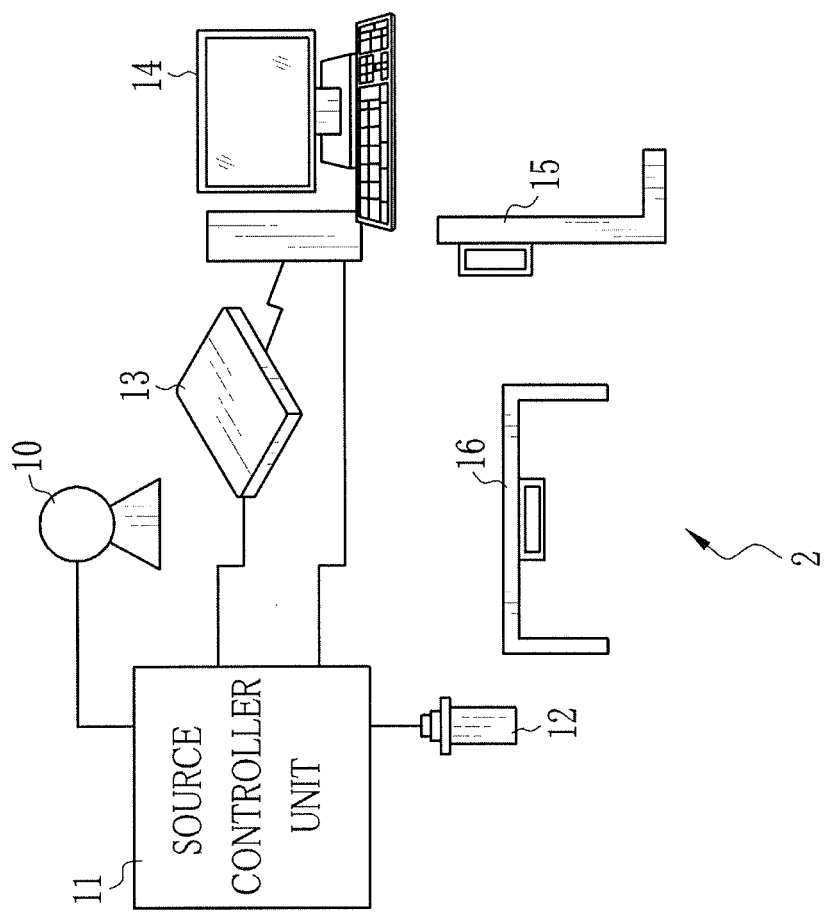
FIG. 1 is a diagram schematically illustrating an x-ray radiography system.

In FIG. 1, a radiography system 2 includes an x-ray source 10, a source controller unit 11 for controlling the x-ray source 10, an activator switch 12 for instructing a start of radiation from the x-ray source 10, an electronic cassette 13 as a radiographic image detector, a console 14 for controlling operation of the electronic cassette 13 and processing x-ray images acquired through the electronic cassette 13, a radiographic stand 15 for imaging a subject in the standing posture and a radiographic table 16 for imaging a subject lying thereon. The x-ray source 10, the source controller unit 11 and the activator switch 12 constitute an x-ray projector, whereas the electronic cassette 13 and the console 14 constitute an x-ray imaging apparatus. The radiography system 2 further includes a source positioning mechanism for setting the x-ray source 10 to a designated position in a designated direction and other equipment, although they are not shown in the drawings. The source controller unit 11 may be integrated into the console 14.

The x-ray source 10 has an x-ray tube for radiating x-rays and a collimator for limiting the irradiation field of x-rays from the x-ray tube. The x-ray tube has a cathode which includes a filament for emitting thermions and an anode (target) against which the thermions strike to radiate x-rays. The collimator may for example be made of lead plates, which shield x-rays and are assembled into a double-cross formation having a center aperture for letting x-rays pass through it. The lead plates are movable so as to change the size of the center aperture to confine the irradiation field to a suitable range.

Figure 2:
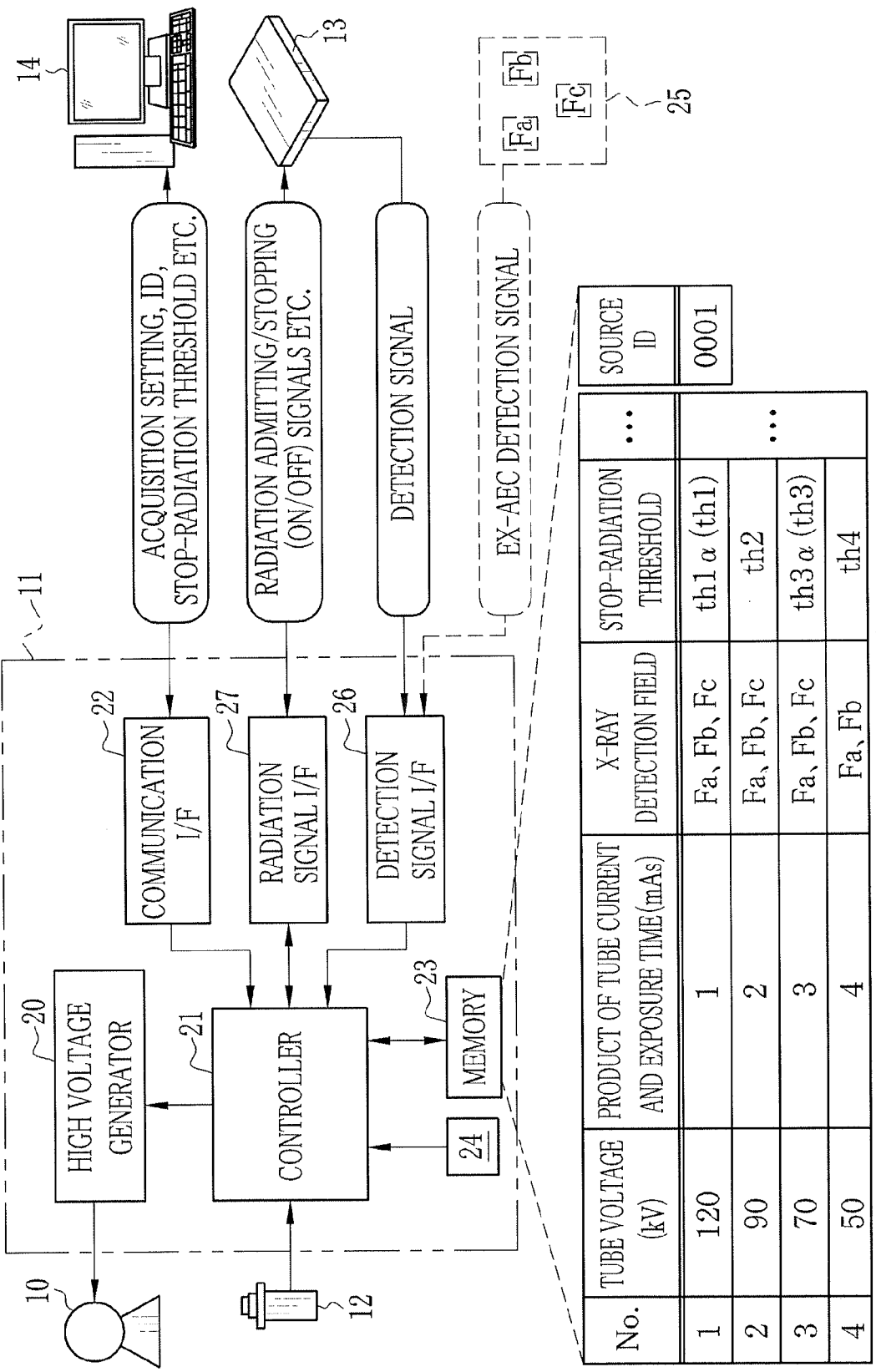
FIG. 2 is an explanatory diagram illustrating an internal structure of a source controller unit and connections between the source controller unit and other devices.

As shown in FIG. 2, the source controller unit 11 includes a high voltage generator 20 for supplying a high voltage to the x-ray source 10, a controller 21 for controlling tube voltage, tube current and x-ray radiation time, and a communication interface (I/F) 22. The high voltage generator generates a high tube voltage by boosting an input voltage through a transducer, and supplies the tube voltage as the driving power to the x-ray source 10 through a high voltage cable. The tube voltage determines energy spectra of x-rays from the x-ray source 10, and the tube current determines the amount of radiation per unit time.

The controller 21 is connected to the activator switch 12, a memory 23 and a touch panel 24. The activator switch 12, which is operated by a radiologist, may be a two-step push button switch that outputs a warm-up start signal for staring warming up the x-ray source 10 upon being pushed to the first step. Thereafter, upon being pushed further to the second step, the activator switch 12 outputs a radiation starting signal for letting the x-ray source 10 start radiation. These signals are fed through a signal cable to the source controller unit 11. The controller 21 starts supplying power from the high voltage generator 20 to the x-ray source 10 upon receipt of the radiation starting signal from the activator switch 12.

The memory 23 previously stores several options of image acquisition settings, each option including tube voltage, mAs value (a product of tube current and x-ray exposure time), and etc. In the present embodiment, four kinds of options are stored in the memory 23; first to fourth tube voltage levels: 120 kV, 90 kV, 70 kV and 50 kV, are associated with the respective mAs values, respective detection fields of an existing AEC sensor 25, which are attached to the x-ray source 10, and respective threshold levels to be compared with an integrated value of detection signals from the existing AEC sensor 25. The detection signals from the existing AEC sensor 25, hereinafter referred to as ex-AEC detection signals, may be voltage levels representative of incident amounts of x-rays. Through comparison of the integrated value of existing AEC detection signals with an appropriate one of the threshold levels, the controller 21 makes a decision to stop x-ray radiation. As criteria for the decision to stop radiation, hereinafter referred to as stop-radiation thresholds, default values th1 to th4 may be preset in the memory 23 before the shipment of the x-ray source 10.

The image acquisition settings may be manually set by a radiologist or operator through the touch panel 24, for example, by designating the number of one of the stored image acquisition settings. As shown in the first or the third option assigning the tube voltage of 120 kV or 70 kV, respectively, the default value may be modified by the operator, and then both the modified value and the default value will be memorized and get available afterward. Once the number of the image acquisition settings is designated, the source controller unit 11 controls the x-ray source 10 to radiate x-rays under the designated imaging conditions corresponding to the tube voltage and the product of tube current and exposure time. The source controller unit 11 is also provided with an AEC function, by which an operation to interrupt the radiation is carried out when it is detected that the projected amount of x-rays gets to a sufficient level, even before the current product of tube current and exposure time reaches the preset value designated as one image acquisition setting, i.e. even before the designated exposure time is over. In order to avoid the risk of underexposure, the product of tube current and exposure time (or the exposure time) to be preset in the memory 23 should be a maximum available value in every option of the image acquisition settings. Thus, the source controller unit 11 will not terminate the radiation before a decision to stop radiation is made through the AEC function when the actual radiation dose has reached a sufficient amount.

The memory 23 further stores an identification data given to each individual x-ray source 10, called source ID. The controller 21, as being communicably connected to the console 14, reads out the source ID along with the stop-radiation threshold from the memory 23, and transmits the source ID to the console 14.

The existing AEC sensor 25 may be a conventional ion chamber or the like, which outputs ex-AEC detection signals corresponding to the incident amount of x-rays. The ex-AEC sensor 25 has a planer size that is approximately equal to that of an imaging cassette available for the radiography system 2, so that the ex-AEC sensor 25 may serve for measuring x-rays in front of the imaging surface of the cassette. The ex-AEC sensor 25 is provided with three detection fields Fa, Fb and Fc: upper right and upper left detection fields being opposed to lungs of the human subject for chest-imaging, and a lower center detection field. The image acquisition settings, as shown in FIG. 2, includes an item for designating which of the detection fields Fa to Fc should be adopted.

The ex-AEC sensor 25 is connected to a detection signal interface 26, so that the x-AEC detection signals are transmitted to the controller 21 through the detection signal interface 26. The controller 21 may receive an integrated value of the x-AEC detection signals if the ex-AEC sensor 25 has an integrator circuit. If not, the controller 21 may directly receive the x-AEC detection signal (an instantaneous value) from the ex-AEC sensor 25. If the ex-AEC sensor 25 does not have any integrator circuit, the controller 21 should be provided with an integrator circuit, so that the x-AEC detection signals may be integrated inside the controller 21. A first embodiment will be described on the assumption that the ex-AEC sensor 25 is provided with an integrator circuit and the controller 21 does not include any integrator circuit, so that the controller 21 is fed with the integrated value of the x-AEC detection signals. Note that the ex-AEC sensor 25 may output an instantaneous value of the x-AEC detection signal or an integrated value of the x-AEC detection signals from each individual x-ray detection field, or the sum or the average of the x-AEC detection signals from the respective x-ray detection fields.

The controller 21 starts monitoring the integrated value of the x-AEC detection signals upon receipt of a radiation starting signal from the activator switch 12, comparing the integrated value with the stop-radiation threshold, given as one image acquisition setting, at appropriate intervals. When the integrated value reaches the stop-radiation threshold as a result of continuous x-ray radiation from the x-ray source 10, the controller 21 outputs a radiation ending signal to the high-voltage generator 20. In response to the radiation ending signal, the high-voltage generator 20 stops power supply to the x-ray source 10, deactivating the x-ray source 10 to stop x-ray radiation.

Unlike the communication interface 22 or the detection signal interface 26, a radiation signal interface 27 may be provided in the source controller unit 11 in such an embodiment where the time to start x-ray radiation or the time to stop x-ray radiation is determined according to other kinds AEC signals than the above-mentioned ex-AEC signals, i.e. voltage levels from the ex-AEC sensor 25. The radiation signal interface 27 should be connected either to an AEC sensor that has an equivalent function to the ex-AEC sensor 25 and the controller 21 or to such an electronic cassette as the electronic cassette 13 of the present embodiment, which has an equivalent function to the ex-AEC sensor 25 and the controller 21, as set forth in detail below.

In the embodiment where the radiation signal interface 27 is connected to an electronic cassette having an equivalent function to the ex-AEC sensor 25 and the controller 21, the controller 21 sends an inquiry signal to the electronic cassette 13 through the radiation signal interface 27 when the controller 21 receives the warm-up start signal from the activator switch 12. Upon receipt of the inquiry signal, the electronic cassette begins to prepare for imaging, terminating charge-resetting operation and getting ready for a charge accumulating operation, in a manner as set forth later. Then the electronic cassette sends back a radiation admitting signal to the controller 21 as a response to the inquiry signal. When the controller 21 receives both the radiation admitting signal through the radiation signal interface 27 and the radiation starting signal from the activator switch 12, the controller 21 drives the high-voltage generator 20 to start supplying the x-ray source 10. When the controller 21 receives a radiation stopping signal from an AEC sensor or the electronic cassette having an equivalent function to the ex-AEC sensor 25 and the controller 21 through the radiation signal interface 27, the controller 21 stops the power supply from the high-voltage generator 20 to the x-ray source 10 to deactivate the x-ray source 10. Although the electronic cassette 13 is connected to the detection signal interface 26 and the radiation signal interface 27 in the drawings, either the detection signal interface 26 or the radiation signal interface 27 is alternatively used for the radiation stopping process in practice.

Figure 3:
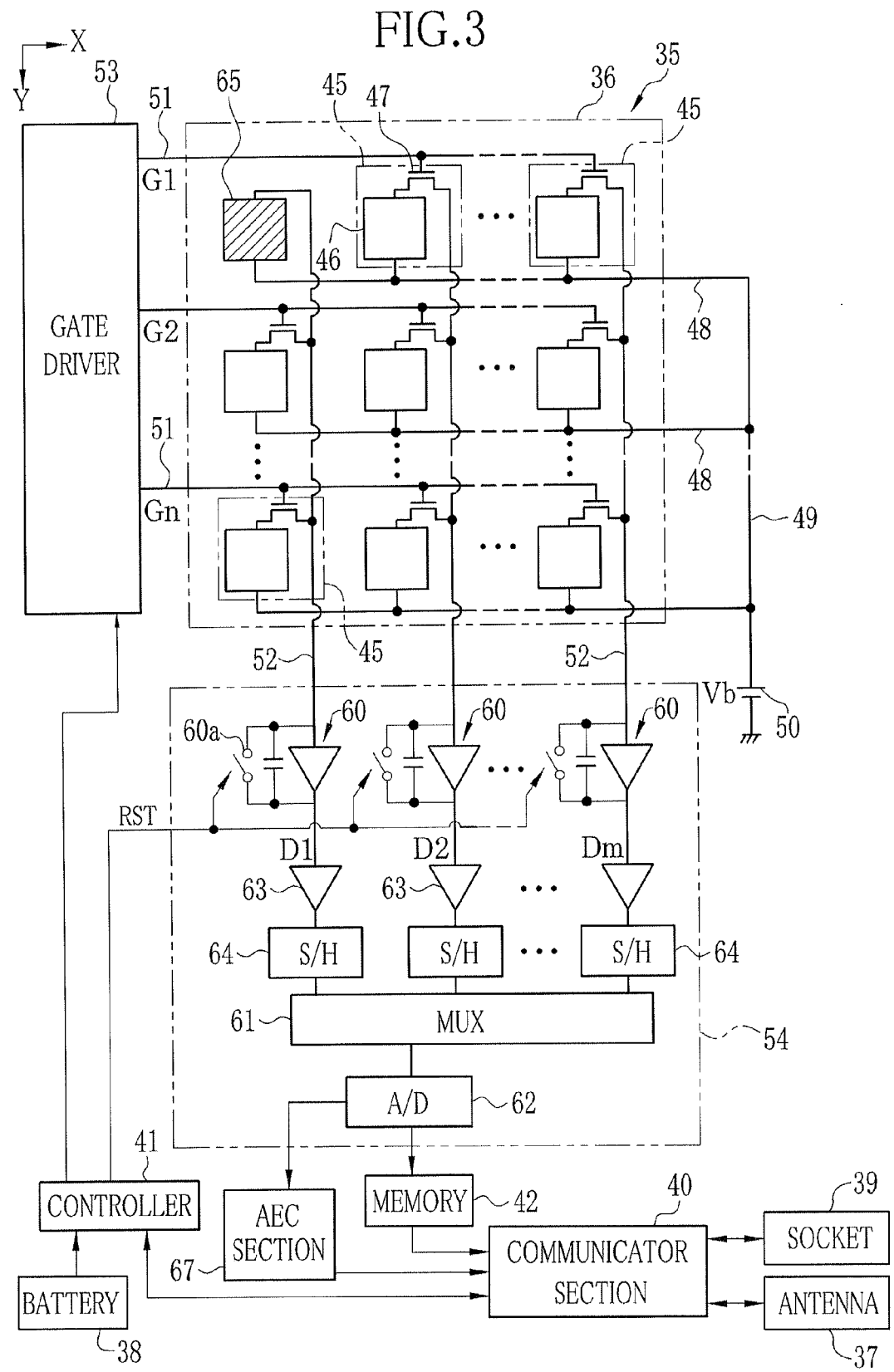
FIG. 3 is a block diagram illustrating an internal structure of an electronic cassette.

Referring to FIG. 3, an internal structure of the electronic cassette 13 will be described. As well-known in the art, the electronic cassette 13 mainly consists of a flat panel detector (FPD) 35 and a housing containing the FPD 35. The housing of the electronic cassette 13 has a flat planer body having a plane size approximately equal to that of radiographic film cassettes and IP cassettes (imaging plate cassettes) which may also be called computed radiography cassettes (CR cassette), dimensioned according to ISO 4090:2001 standard. Therefore, the electronic cassette 13 can be mounted to a conventional radiographic stand or table which is adapted to the radiographic cassettes like film cassettes and IP cassettes.

Generally, more than one electronic cassette 13 is disposed for one radiography system 2. For example, two electronic cassettes 13 are disposed respectively for the radiographic stand 15 and the radiographic table 16 in each x-ray room. The electronic cassette 13 can be detachably attached to the radiographic stand 15 or table 16. Besides being used in the radiographic stand 15 or the radiographic table 16, the electronic cassette 13 may be used independently. For example, the electronic cassette 13 may be put directly on a bed on which the subject is lying, or may be held by the subject.

The electronic cassette 13 has an antenna 37 and a battery 38 incorporated therein, permitting wireless communication with the console 14. The antenna 37 transmits electric waves for wireless communication with the console 14. The battery 38 supplies power for actuating components of the electronic cassette 13. The battery 38 should be of a smaller size for the sake of compactness of the thin electronic cassette 13. The battery 38 may be rechargeable using an external specific charging device, called cradle. The battery 38 may also be configured to be capable of being wirelessly power-supplied.

In addition to the antenna 37, the electronic cassette 13 is provided with a socket 39. The socket 39 is used for wired connection to the console 14 when the wireless communication between the electronic cassette 13 and the console 14 is not available, for example, because of the run-out of the battery 38. When a cable from the console 14 is connected to the socket 39, the electronic cassette 13 can communicate with the console 14 through the cable, and may also be power-supplied from the console 14.

The antenna 37 and the socket 39 are connected to a communicator section 40. The communicator section 40 mediates transmission of various data, including image data, between the antenna 37 and the socket 39 and a controller 41 and a memory 42.

The FPD 35 has a thin film transistor (TFT) active matrix substrate with an imaging area 36 formed thereon. The imaging area 36 is constituted of an array of pixels 45 for accumulating signal charges according to the incident amount of x-rays. The pixels 45 are arranged in a matrix (n-lines and m-columns) at predetermined intervals; the line direction and the column direction of the pixel matrix correspond to x-direction and y-direction of the imaging area 36, respectively.

The FPD 35 may be of an indirect conversion type that has a not-shown scintillator (a phosphorous member) for converting x-rays to visible rays and converts the visible rays to electric charges through the pixels 45. The scintillator is positioned to face to the whole imaging area 36. The scintillator is made of a phosphor such as cesium iodide (CsI) or gadolinium oxy sulfide (GOS). Note that the scintillator and the FPD 35 may be arranged in the PSS (penetration side sampling) style, wherein the scintillator and the FPD 35 are arranged in this order from the direction in which the x-rays are incident, or may be arranged in the ISS (irradiation side sampling) style, wherein the FPD 35 and the scintillator are arranged in the opposite order. The FPD 35 may also be of a direct conversion type flat panel detector using a conversion layer that converts x-rays directly to electric charges (the conversion layer may for example be made of amorphous selenium).

Each of the pixels 45 includes a photodiode 46, a not-shown capacitor, and a thin film transistor (TFT) 43. The photodiode 46 is a photoelectric conversion element that generates charges (pairs of electrons and holes) in response to incident visible light. The capacitor accumulates the charges generated from the photodiodes 46, and the TFT 47 serves as a switching element.

The photodiode 46 has a semiconductor layer, e.g. PIN-type layer, and upper and lower electrodes, which are provided on the top and bottom of the semiconductor layer. The photodiode 46 is connected at its lower electrode to the TFT 47 and at its upper electrode to a bias line 48. The bias lines 48 are provided in same number as the number "n" of rows of pixels 45 of the imaging area 36. The bias lines 48 are connected together to an interconnection line 49, which is connected to a bias power source 50. Through the interconnection line 49 and the bias lines 48, a bias voltage Vb is applied to the upper electrodes of the photodiodes 46. The applied bias voltage Vb induces an electric field in the semiconductor layer of each photodiode 46. Because of the induced electric field, the electric charges (pairs of electrons and holes) generated through the photoelectric conversion in the semiconductor layer will move to the opposite electrodes; the electrons move to the upper electrode of positive polarity, whereas the holes move to the lower electrode of negative polarity. As a result, electric charges are accumulated in the capacitors.

Each of the TFTs 47 is connected at its gate to a scanning line 51, at its source to a signal line 52, and at its drain to the photodiode 46. The scanning lines 51 and the signal lines 52 are interconnected into a grid. The scanning lines 51 are provided for the respective rows (n-rows) of pixels 45 of the imaging area 36 such that the scanning lines 51 are individually connected to one row of pixels 45. The signal lines 52 are provided for the respective columns (m-columns) of pixels 45 of the imaging area 36 such that the signal lines 52 are individually connected to one column of pixels 45. The scanning lines 51 are connected in parallel to the gate driver 53, whereas the signal lines 52 are connected in parallel to the signal processing circuit 54.

The gate driver 53 drives the TFTs 47 to make accumulating operation for accumulating the signal charges in the pixels 45, reading operation for reading out the signal charges from the pixels 45, or charge-resetting operation for resetting the signal charges accumulated in the pixels 45. The controller 41 controls the timing of the respective operations executed by the gate driver 53.

The accumulating operation is carried out by turning off the TFTs 47. While the TFT 47 is off, signal charges are accumulated in the pixel 45. In the reading operation, the gate driver 53 sequentially outputs gate pulses G1 to Gn, one gate pulse to one scanning line 51, thereby to activate the scanning 51 one after another. Thus, the TFTs 47 of the activated scanning line 51 are turned on line by line. When the TFTs 47 of one line are turned on, the signal charges accumulated in the pixels 45 of this line are fed through the respective signal lines 52 to the signal processing circuit 54.

The signal processing circuit 54 includes integrating amplifiers 60, a multiplexer (MUX) 50 and an A/D converter 51. The integrating amplifiers 60 are connected to the signal lines 52 in one-to-one relationship. Each integrating amplifier 60 consists of an operational amplifier and a capacitor connected between an input and an output of the operational amplifier. The signal line 52 is connected to the input of the operational amplifier. The operational amplifier has another input terminal that is grounded. The integrating amplifiers 60 integrate the signal charges from the signal lines 52 to convert them to the voltage signals D1 to Dm. An output terminal of the individual integrating amplifier 60 is connected through an amplifier 63 and a sampling-and-holding circuit (S/H) 64 to a common multiplexer (MUX) 61, and an A/D converter 62 is connected to an output of the MUX 61.

The MUX 61 sequentially selects one of the integrating amplifiers 60 after another to feed the voltage signals D1 to Dm from the integrating amplifiers 60 serially to the A/D converter 62. The A/D converter 62 converts the analog voltage signals D1 to Dm to digital pixel levels corresponding to their signal levels. An additional amplifier may also be connected in between the MUX 61 and the A/D converter 62.

In the reading operation after the charge accumulating operation, the gate pulses G1 to Gn sequentially turn on the TFTs 47 line by line, feeding the signal charges from the capacitors of the pixels 45 of the activated line through the signal lines 52 to the integrating amplifiers 60. When the MUX 61 has read out voltage signals D1 to Dm for one line from the integrating amplifiers 60, the controller 41 outputs a reset pulse RST to the integrating amplifiers 60 to turn on the reset switches 60a of the integrating amplifiers 60. Thereby, the signal charges for one line, accumulated in the integrating amplifiers 60, are reset to zero. After resetting the integrating amplifiers 60, the controller 41 lets the gate driver 53 output the gate pulse to the next line, starting reading the signal charges from the pixels 45 of the next line. These operations are sequentially repeated to read out the signal charges from all pixels 45 line by line.

When the signal charges have been read out from all lines, image data of a frame of x-ray image is stored in the memory 42. The image data is read out from the memory 42 and transmitted to the console 14 through the communicator section 40. Thus the x-ray image of the subject is detected.

As well known in the art, dark charges will be generated in the semiconductor layer of the photodiodes 46 regardless of whether x-rays are incident or not. The dark charges will be accumulated in the capacitor of each pixel 45 as the bias voltage Vb is applied. Since the dark charges will effect as a noise component to image data, these dark charges are eliminated by the charge-resetting operation. That is, the dark charges are swept off the pixels 45 through the signal lines 52.

The resetting operation may be executed for example according to a line-sequential method, whereby the pixels 39 are to be reset line by line. According to the line-sequential resetting method, the gate driver 53 sequentially outputs the gate pulses G1 to Gn to the respective scanning lines 51, like in the reading operation, to turn on the TFTs 47 line by line. As the TFTs 42 are turned on, the dark charges accumulated in the pixels 45 are discharged through the signal lines 52 to the integrating amplifiers 60. However, unlike the reading operation, the MUX 61 does not read out the charges accumulated in the integrating amplifiers 60 in the resetting operation. Instead, the controller 41 outputs the reset pulses RST synchronously with the respective gate pulses G1 to Gn, to reset the integrating amplifiers 60.

The charge-resetting operation may also be carried out according to a parallel resetting method or an allover resetting method. According to the parallel resetting method, pixel lines are subdivided into groups, and the dark charges are cleared off the pixels line by line within the respective groups in parallel to other groups. According to the allover resetting method, the gate pulses are simultaneously applied to all lines to sweep the dark charges off all pixels at once. These methods may speed the charge resetting operation.

In the embodiment having the radiation signal interface 27, the controller 41 of the electronic cassette 13 controls the FPD 35 to make the resetting operation upon receipt of the inquiry signal from the controller 21 of the source controller unit 11, and then sends back the radiation admitting signal to the source controller unit 11. Thereafter, upon receipt of a radiation starting signal, the controller 41 controls the FPD 35 to proceed from the resetting operation to the accumulating operation. In an embodiment without the radiation signal interface 27, the FPD 35 detects the start of x-ray radiation using later-mentioned detective pixels 65 while repeating the resetting operation. When the start of x-ray radiation is detected, the controller 41 controls the FPD 35 to proceed from the resetting operation to the accumulating operation. Thereafter when an end of x-ray radiation is detected using the detective pixels 65, the controller 41 controls the FPD 35 to proceed from the accumulating operation to the reading operation.

Besides the pixels 45, which are connected to the signal lines 52 through the TFT 47 in the way as described above, those detective pixels 65 are provided in the same imaging area 36 of the FPD 35, which are short-circuited or connected directly to the signal lines 52 without the interconnection of the TFT 47. The detective pixels 65 are used for measuring the amount of x-rays incident on the imaging area 36, serving as a radiation start detecting sensor or a radiation end detecting sensor and an AEC sensor. The detective pixels 65 take up several percent of all pixels within the imaging area 36.

Figure 4:
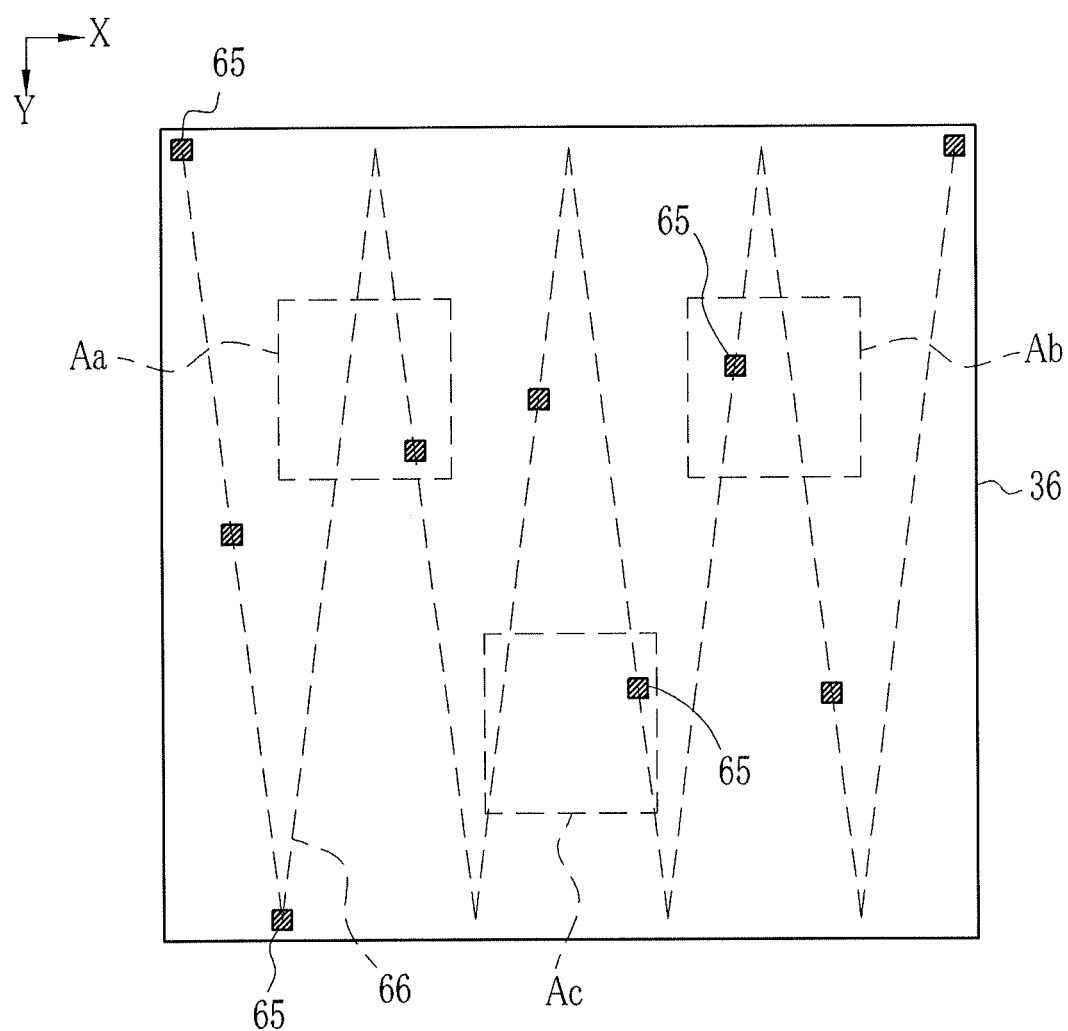
FIG. 4 is an explanatory diagram illustrating a layout of detective pixels in a flat panel detector of the electronic cassette.

As shown in FIG. 4, the detective pixels 65 are arranged along a wave-formed track 66, as shown by dotted lines, which is symmetrical to a center line extending in the y-direction of the imaging area 36, such that the detective pixels 65 are distributed evenly over the whole imaging area 36. The detective pixels 65 are provided one in every third or fourth column of pixels 45, being connected to the same signal line 52 in each of these columns. The locations of the detective pixels 65 are known while the FPD 35 is being manufactured, so that the locations of all detective pixels 65 are previously memorized as coordinate values in a not-shown non-volatile memory of the FPD 35.

As the detective pixels 65 are directly connected to the signal lines 52 without interconnection of the TFTs 47, the electric charges generated in the detective pixels 65 are immediately read into the signal lines 52, even during the accumulating operation while the TFTs 47 of the ordinary pixels 45 are off. Accordingly, the electric charges generated from the detective pixels 65 will always flow into those integrating amplifiers 60 which are connected to the detective pixels 65 through the signal lines 52.

Figure 5:
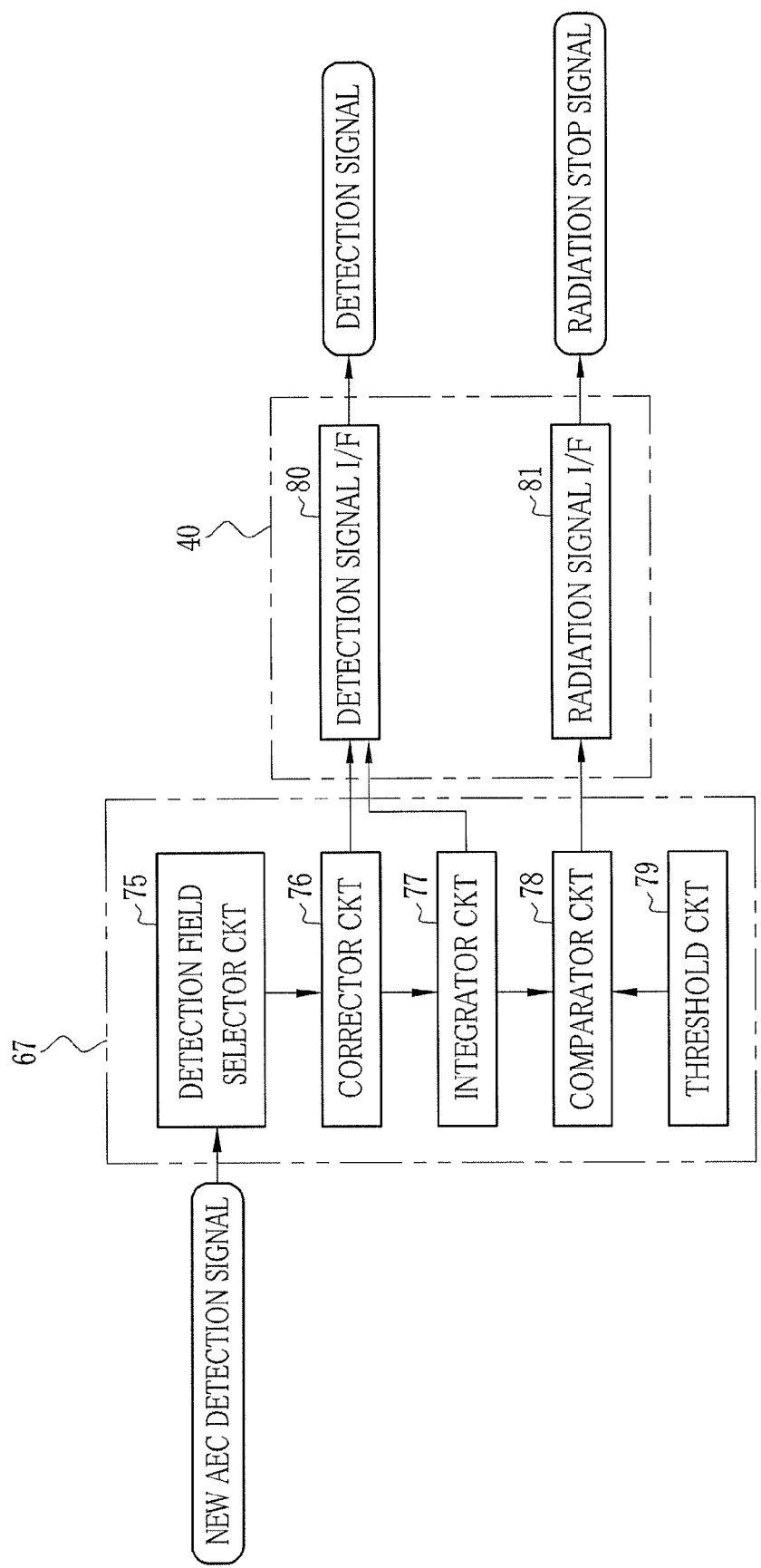
FIG. 5 is a block diagram illustrating internal structures of an automatic exposure control (AEC) section and a communicator section of the electronic cassette.

Voltage levels corresponding to the electric charges from the detective pixels 65, hereinafter referred to as new AEC detection signals, are taken into an automatic exposure control (AEC) section 67 through the A/D converter 62, the AEC section 67 being provided in the electronic cassette 13 (see FIG. 3). Referring to FIG. 5, the AEC section 67 of the electronic cassette 13 includes a detection field selector circuit 75, a corrector circuit 76, an integrator circuit 77, a comparator circuit 78 and a threshold circuit 79. Besides these components, the AEC section 67 is provided with a circuit for detecting the start and end of radiation through comparison of the new AEC signals from the detective pixels 65 with predetermined thresholds.

The detection field selector circuit 75 decides which to select for the automatic exposure control among the detective pixels 65 distributed over the imaging area 36. The corrector circuit 76 corrects the new AEC detection signals from the selected detective pixels 65 to equivalent values (detection signals) to the ex-AEC detection signals. The integrator circuit 77 integrates the detection signals. The comparator circuit 78 begins to monitor the integrated value of the detection signals from the integrator circuit 77 upon the start of x-ray radiation being detected, comparing the integrated value with a stop-radiation threshold given by the threshold circuit 79, which may be equal to the stop-radiation threshold given in the source controller unit 11, at appropriate intervals. When the integrated value reaches the threshold, the comparator circuit 78 outputs a radiation-stopping signal.

The communicator section 40 is provided with a detection signal interface 80 and a radiation signal interface 81. The detection signal interface 80 and the radiation signal interface 81 are connected to the detection signal interface 26 and the radiation signal interface 27 of the source controller unit 11 respectively through signal cables. The detection signal interface 80 is connected to the corrector circuit 76 and the integrator circuit 77 of the AEC section 67, so that the detection signal interface 80 selectively outputs the detection signals from the corrector circuit 76, which correspond to the new AEC detection signals, or the integrated value of the detection signals, which is output from the integrator circuit 77. The radiation signal interface 81 is used for receiving the inquiry signal, sending back the radiation admitting signal in response to the inquiry signal, outputting the radiation stopping signal from the comparator circuit 78. Like the source controller unit 11, the detection signal interface 80 and the radiation signal interface 81 are alternatively used in the radiation stopping procedure, not used at the same time.

The console 14 is communicably connected to the electronic cassette 13 through wired or wireless communication devices, to control the electronic cassette 13. Specifically, the console 14 sends data of image acquisition settings to the electronic cassette 13 to set up conditions for signal processing in the FPD 35, e.g. amplification gains of voltage signals corresponding to the accumulated signal charges. The console 14 also controls ON and OFF of the power to the electronic cassette 13, switches over operation modes of the electronic cassette 13, for example, between a power-saving mode and an imaging preparation mode.

The console 14 process the x-ray image data from the electronic cassette 13 for various image-renderings, such as offset correction, gain correction, defect correction etc. The defect correction is to compensate for pixel levels of missing pixels of the image data which correspond to the detective pixels 65 through interpolation using pixel levels adjacent to the missing pixels. The processed x-ray image may be displayed on a monitor 89 (see FIG. 7) of the console 14, and also stored in a storage device 87 or a memory 86 of the console 14 (see FIG. 7), or a storage device like an image database server that the console 14 is connected to through a network.

The console 14 may receive examination orders, each including information on the sex and age of the patient as the test subject, the target site to be imaged, such as head, chest or abdomen, the purpose of imaging, etc., and display the received examination orders on the monitor 89. The examination orders may be issued by external systems, such as a hospital information system (HIS) and a radiological information system (RIS), which manage information on patients and information on radiological examinations. The examination orders may also be manually input by an operator or radiologist. The examination order also includes the imaging direction, such as frontal, lateral, diagonal, posterior-to-anterior (PA), or anterior-to-posterior (AP). The operator checks the content of each examination order on the monitor 89, and input the image acquisition settings according to the examination order through the operation screen of the console 14.

As shown in FIG. 6, the operator may designate more specified image acquisition settings on the console 14, while the source controller unit 11 is merely provided with such image acquisition settings that may be individually predetermined for one tube voltage, which is determined by the target site. Namely, the operator may designate multiple sets of imaging conditions for one tube voltage (target site), e.g. chest PA and chest AP at tube voltage of 120 kV. Moreover, the console 14 memorizes an S value for each set of imaging conditions, the S value being equivalent to the stop-radiation threshold given as one image acquisition setting in the source controller unit 11. The S value is obtained through a histogram analysis of x-ray image data, providing a typical index to the radiation dose like an EI value and an REX value do. Data of the image acquisition settings is stored in a storage device 87.

Figure 7:
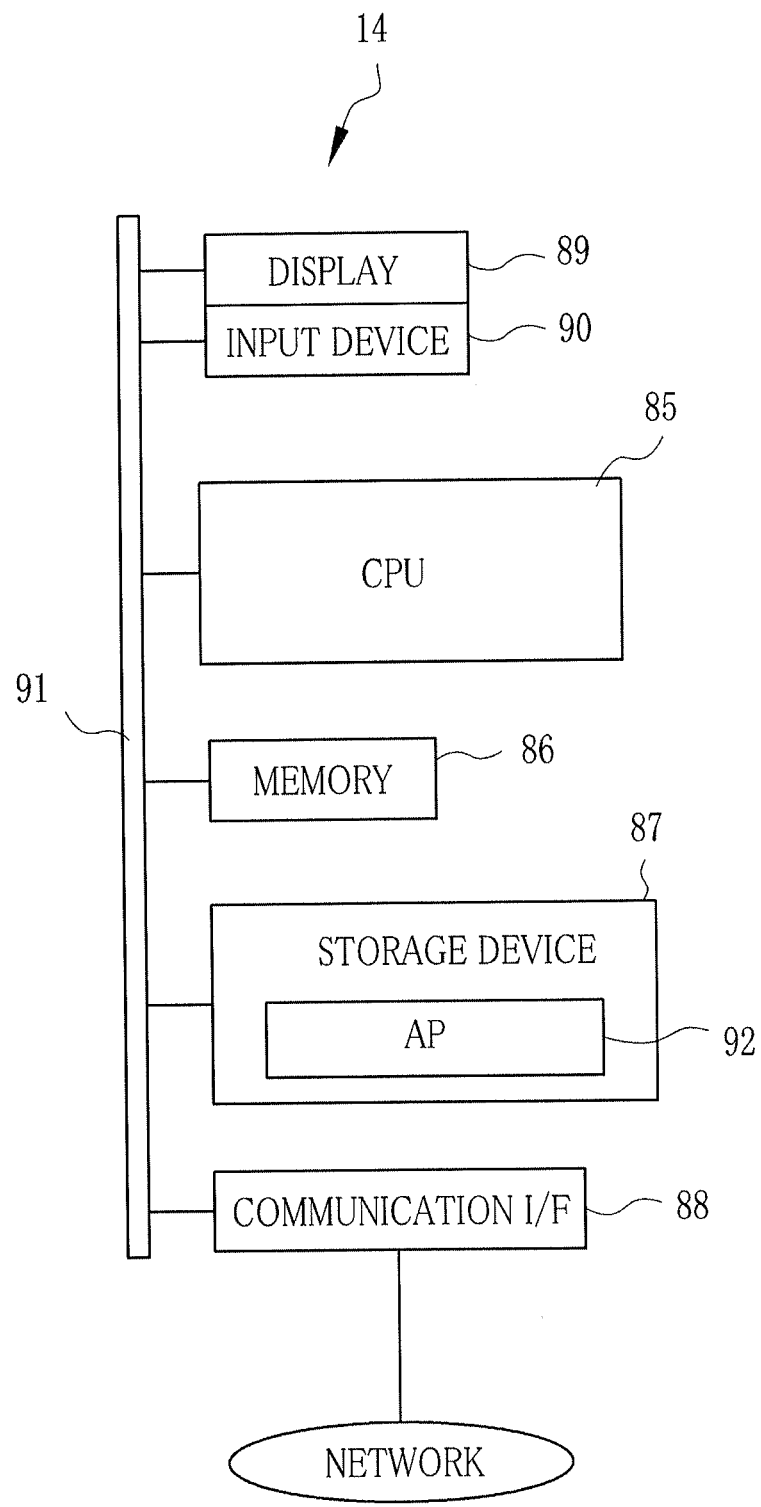
FIG. 7 is a block diagram illustrating an internal structure of the console.

As shown in FIG. 7, the console 14 is configured based on a computer, which includes a CPU 85, the memory 86, the storage device 87, a communication interface (I/F) 88, the monitor 89, and an input device 90. These components are connected to each other via a data bus 47.

The storage device 43 may for example be a hard disc drive built in the main body of the console 14. The storage device 43 stores the control programs and the application programs (AP) 92, which include various programs for the console 14 to execute various radiographic functions, including processing of displaying the examination orders and x-ray images, rendering the x-ray image, and setting up the imaging conditions.

The memory 86 is a work memory for the CPU 85 to execute processing. The CPU 85 carries out procedures according to the control program loaded onto the memory 86 from the storage device 87, to totally control the respective components of the computer while. The communication interface 88 has a network interface that controls data transmission between the console 14 and a external equipment, such as RIS, HIS, the image database server, and the electronic cassette 13. The input device 90 may include a keyboard, a mouse, or a touch panel integrated into the monitor 89.

Referring to FIG. 8, when the AP 92 gets activate, the CPU 85 of the console 14 begins to function as a storage-retrieval processor 95, an input-output controller 96, and a main controller 97. The storage-retrieval processor 95 executes processing for storing various data into the storage device 87 and retrieving various data from the storage device 87. The input-output controller 96 reads out rendering data from the storage device 87 in response to operations by the input device 90, and outputs various operational screens on the monitor 89 on the basis of the read rendering data, the operational screens providing graphical user interfaces (GUI). Moreover, the input-output controller 96 accepts entry of operational commands that may be input on the operational screens using the input device 90. The main controller 97 includes a cassette controller 98 for controlling operations of the electronic cassette 13, and also controls the respective components of the console 14.

The storage device 87 stores source data 99 as shown in FIG. 9. The source data 99 includes regional types of x-ray sources, image acquisition settings and AEC specifications, which are sorted and identified with individual ID numbers.

The regional types indicate whether or not the radiography systems are expected to put priority on installation convenience over other features than installation convenience, such as the quality of radiographic image, classified according to regions in the world, such as Japan, USA, Europe, Asia, etc. Installation procedures for introducing the AEC sensor in place of the ex-AEC sensor 25 and using the radiation signal interface 27 in place of the detection signal interface 26 may take a lot of labor and require certain skills, selecting a suitable connection plug for the new AEC sensor according to the specifications of the source controller unit 11, replacing an existing connection plug with new one, and eventually disabling the function of the detection signal interface 26. Because of the required skills, the installation might not be accomplished in some cases. For this reason, if the priority is put on the installation convenience, the existing AEC sensor 25 and the detection signal interface 26 should rather be used in the same way as in the past, so as not to be contingent on the skill of a worker in charge of the installation. Consequently, the regional types include a installation-priority type for those regions where the skill of workers in charge of installation is relative low or the quality of radiographic images is given a lower priority (see FIG. 10).

On the other hand, as described with reference to FIGS. 2 and 6, once the electronic cassette 13 with the AEC sensor (detective pixels 65) is introduced, the AEC function may be available under various imaging conditions. In contrast, on the side of source controller unit 11, it is hard to designate the imaging conditions in detail because of the limited number of available image acquisition settings. Consequently, the electronic cassette 13 allows the automatic exposure control on the basis of an optimum stop-radiation threshold that is determined depending on specified imaging conditions. That is, it becomes possible to decide the time to stop x-ray radiation on the basis of the stop-radiation threshold suitable for the specified imaging condition, and transmit the radiation stopping signal to the controller 21 through the radiation signal interfaces 81 and 27. As a result, high quality radiographic images will be acquired and other advantages than the installation convenience will be achieved. Therefore, to those regions where workers in charge of installation generally have sufficient skills or where higher priority should be given to the quality of radiographic images and other advantages rather than the installation convenience of the radiography system, a non-installation-priority type is assigned (see also FIG. 10).

The image acquisition settings stored as the source data 99 are equal to those stored in the source controller unit 11 of each x-ray source, except the stop-radiation thresholds, which may be modified by the operators. The AEC specifications include various items, such as presence or absence of an integrator circuit for integrating the AEC detection signals, locations of the x-ray detection fields, which are expressed by x-y coordinates (a pair of x-y coordinates indicating two vertices connected with a diagonal line in the case of a rectangular x-ray detection field), and which value should be output for the automatic exposure control, individual values of the detection signals from the detection fields, the sum or the average of the detection signals from the respective detection fields. The x-y coordinates of the x-ray detection field correspond to locations of the pixels 45, including the detective pixels 65, in the imaging area 36 of the electronic cassette 13; the x-axis of the coordinate system corresponds to the x-direction parallel to the scanning lines 51, the y-axis corresponds to the y-direction parallel to the signal lines 52, and the origin (0, 0) of the coordinate system corresponds to an upper-leftmost pixel 45 in the imaging area 36.

The source data 99 also includes correction data, which represents correlations between new AEC detection signals and ex-AEC signals respectively obtained at different tube voltages to the individual x-ray sources. The correction data is stored in the form of a data table or a function.

Since the ex-AEC sensor 25 is disposed for use in front of an imaging surface of a cassette, the ex-AEC sensor 25 itself will absorb or attenuate the x-rays before being incident on the cassette. Therefore, the stop-radiation threshold for the ex-AEC sensor 25 should be set at such a value for obtaining a necessary dose for acquiring adequate quality of images, taking account of the absorbed amount of x-rays into the ex-AEC sensor 25 itself. On the other hand, while the detective pixels 65 of the electronic cassette 13 are serving as the new AEC sensor, there are intervening parts like the housing of the electronic cassette 13 between the x-ray source and the electronic cassette 13. As for the PSS type electronic cassette 13, where the scintillator and the FPD 35 are laid on one another in this order from the x-ray incident side, the scintillator is included in the intervening parts, whereas the scintillator is not an intervening part in the ISS type. The same applies to such a case where a grid is disposed between the x-ray source 10 and the electronic cassette 13 at the same time when the electronic cassette 13 is introduced, so that the grid may eliminate those x-ray components which are diffused inside the test subject. Because of such intervening parts, the new AEC detection signal from the detective pixels 65 of the electronic cassette 13 may take a lower level than the ex-AEC detection signal to the same amount of radiation dose; the level of the new AEC detection signal can be 80% of the level of the ex-AEC detection signal at the same amount of radiation dose.

Moreover, there may be a difference in range format between the ex-AEC detection signal and the new AEC detection signal; for example, the ex-AEC detection signal may be expressed in a range of minus 5 V to plus 5 V, while the new AEC detection signal may be expressed in a range of 0 mV to 5 mV. For this reason, it is necessary to decide which should be used, the new AEC sensor or the existing AEC sensor, and know what value the new AEC detection signal would have if it is converted to the ex-AEC detection signal taking account of the difference resulted from the intervening parts between the x-ray source and the new AEC sensor as well as the difference in range format between the new AEC detection signal and the ex-AEC detection signal. The correction data is just used to know what value the new AEC detection signal would have in the format of the ex-AEC detection signal, cancelling these differences. The correction data is previously obtained through experiments and simulations, comparing the previously used apparatus, e.g. the ex-AEC sensor 25, with an introduced apparatus, e.g. the electronic cassette 13, particularly as to whether the introduced cassette is of PSS type or ISS type, whether it includes a scintillator or not, what material is used for the scintillator, whether a grid is provided or not, etc. Whether the scintillator as one intervening part exits or not may be determined from the specifications on the electronic cassette 13 as to whether the electronic cassette 13 is of PSS type or ISS type. Data as to whether the grid is provided or not may be input through a graphic use interface (GUI) on the monitor 89 of the console 14. Aside from the intervening parts, because the principle of x-ray detection by the new AEC sensor differs from that by the existing or conventional AEC sensor, the respective sensors will detect different values in response to the same radiation dose. Also the difference between the detected values, due to the difference in detection principle, may be canceled by means of the correction data, which may be obtained through experiments and simulations.

The source data 99 may be revised automatically with the latest data that may be distributed over the network each time a new type x-ray source is released. The source data 99 may also be manually revised by operating the input device 90 on the basis of information on those x-ray sources which may probably be used in the radiography system, the information being available from the respective manufacturers.

Referring now to FIGS. 10 to 14, the operation of the first embodiment will be described with respect to a case where previously used cassette and console are replaced with the electronic cassette 13 and the console 14, and the detective pixels 65 of the electronic cassette 13 are used as the new AEC sensor instead of the ex-AEC sensor 25 attached to the x-ray source 10.

Figure 14A:
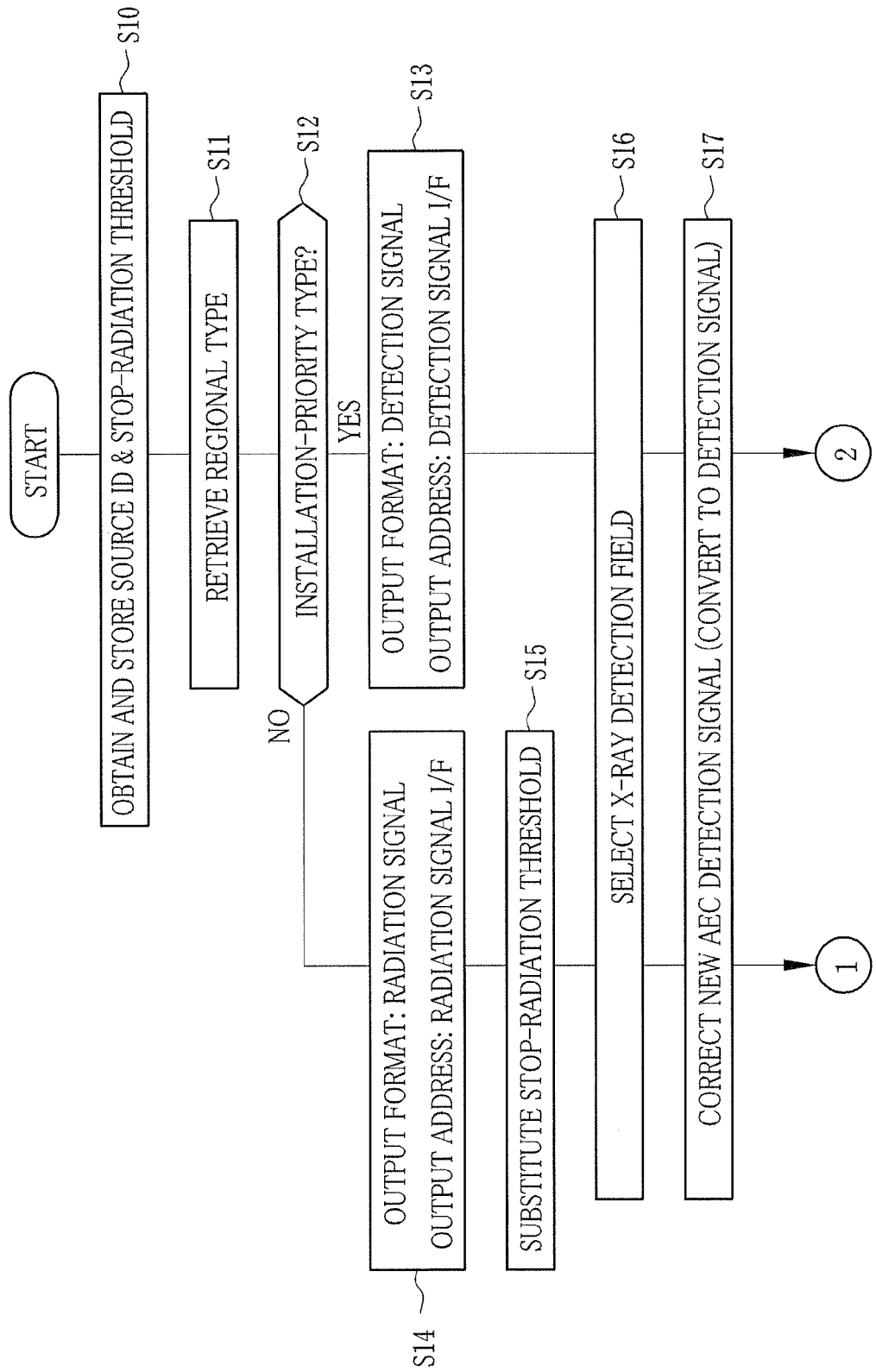
FIGS. 14A and 14B show a flowchart illustrating an operation sequence of the communicator section and the AEC section.
Figure 14B:
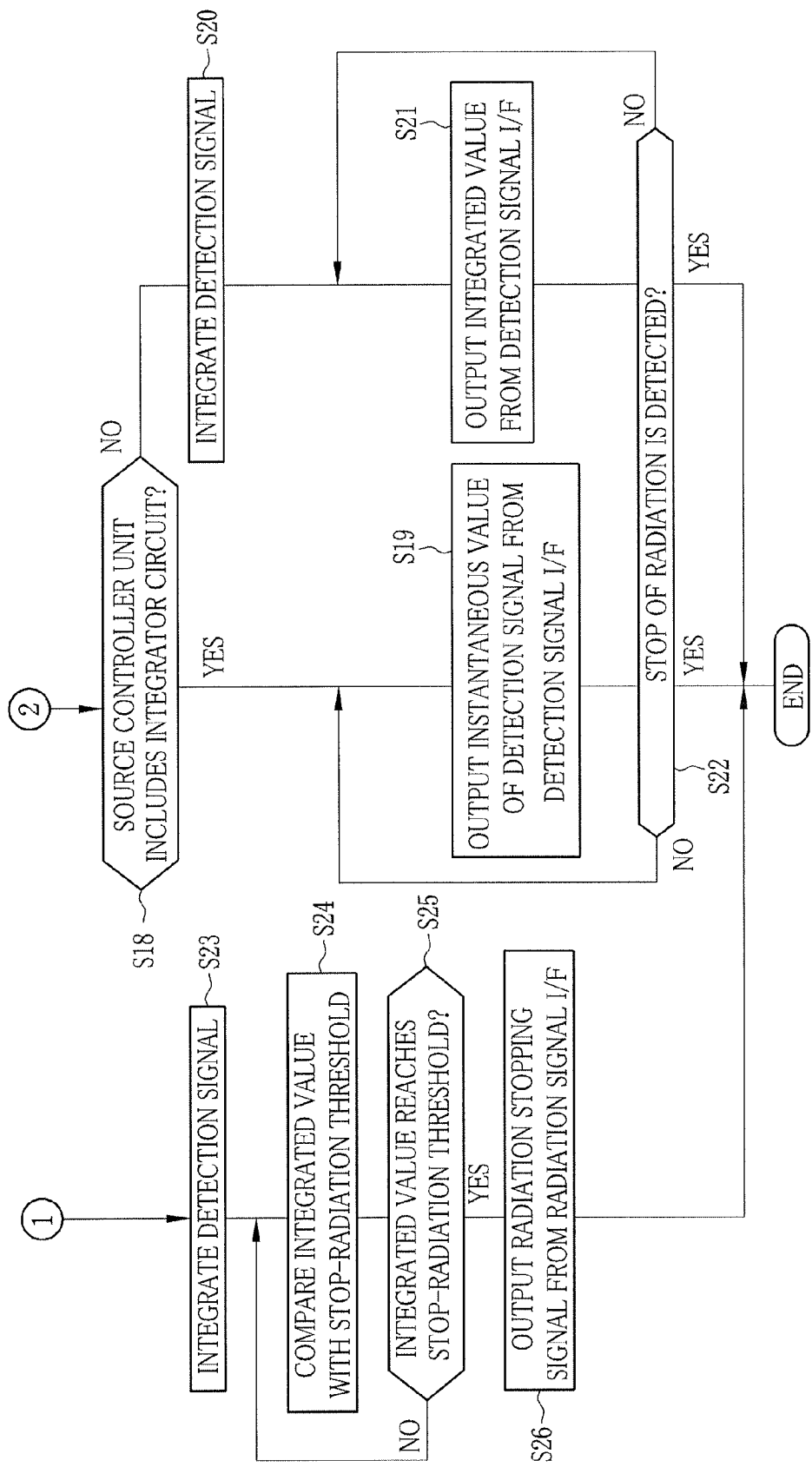

As shown in the flowchart of FIG. 14A, the storage-retrieval processor 95 of the CPU 85 of the console 14 (see FIGS. 7 and 8) has data on the source ID and the stop-radiation threshold stored in the storage device 87 when these data pieces are transmitted from the source controller unit 11 through the communication interface 22 after the communication path to the source controller unit 11 is established (step: S10). Then the storage-retrieval processor 95 retrieves a regional type from the source data 99 in accordance with the received source ID from the source controller unit 11 and the region reset at the shipment (S11). In addition, the storage-retrieval processor 95 retrieves those image acquisition settings, AEC specifications and correction data corresponding to the received source ID. The retrieved data are transferred along with the data on stop-radiation threshold to the cassette controller 98 and then to the electronic cassette 13.

[Selecting Output Address and Output Format]

On the basis of the regional type data from the console 14, the controller 41 of the electronic cassette 13 selects an output address and an output format of those signals used for the automatic exposure control. Specifically, as shown in FIG. 10, if the regional type is the installation-priority type ("Yes" in step S12), the output address is selected to be the detection signal interface 80 of the communicator section 40 (see FIGS. 3 and 5), and the output format is selected to be the detection signal (S13). If, on the other hand, the regional type is the non-installation-priority type ("No" in step S12), the output address is selected to be the radiation signal interface 81 of the communicator section 40, and the output format is selected to be the radiation signal (S14). In the former case, the output format is specified in more detail on the basis of the AEC specifications, which indicates the presence or absence of the integrator circuit and instructs which value to output, individual values or the sum or the average of the detection signals from the respective detection fields.

[Adjusting Location of Detection Field]

With reference to the location data of the detection fields of the ex-AEC sensor 25, which is fed from the console 14 to the detection field selector circuit 75 of the AEC section 67 (see FIGS. 3 and 5), the detection field selector circuit 75 selects from among the new AEC detection signals detected by all detective pixels 65 of the electronic cassette 13 those new AEC detection signals which are from those detective pixels 65 located in corresponding areas to the detection fields of the ex-AEC sensor 25. Then the detection field selector circuit 75 outputs the selected new AEC detection signals to the corrector circuit 76 (S16). For instance, when the received source ID is "0001" of FIG. 9, the detection field selector circuit 75 selects the new AEC signals from the detective pixels 65 exiting in areas Aa, Ab and Ac corresponding to the detection fields Fa, Fb and Fc of the ex-AEC sensor 25, respectively.

[Adjusting Detection Field to Cassette Posture]

Since the electronic cassette may be used in various postures for radiography, there may be cases where the detection fields (the detective pixels 65) of the electronic cassette 13, as selected only on the basis of the location data of the detection fields of the ex-AEC sensor 25, do not actually correspond to the detection fields of the ex-AEC sensor 25 because of the different mounting posture of the cassette. In order to avoid this problem, it is preferable for the detection field selector circuit 75 to select the detection field on the basis of information about the mounting posture of the electronic cassette in addition to the location data of the detection fields of the ex-AEC sensor 25. The mounting posture of the electronic cassette may be detected for example by a photosensor like as disclosed in JPA 2011-067314.

More specifically, provided that the location data of the detection fields of the ex-AEC sensor 25 represents ones in a vertical mounting posture of the ex-AEC sensor 25, if the electronic cassette is mounted in a lateral posture, the location data (coordinate values) of the detection fields of the ex-AEC sensor 25 is put in use after being turned by an angle of 90 degrees or 270 degrees about the center of the cassette imaging surface. Alternatively, the source data 99 may include two kinds of location data of the detection fields of the ex-AEC sensor 25 prepared for the vertical mounting posture and the lateral mounting posture, so that either of the location data may be selected according to the detected mounting posture of the cassette.

[Correcting Detection Signal]

The corrector circuit 76 converts the new AEC detection signals, as received from the detection field selector circuit 75, to the detection signals, using suitable correction data for the current image acquisition settings, particularly the current tube voltage (S17). On the basis of the data instructing the output format of the detection signals, i.e. whether to output values detected from the individual detection fields or the sum or the average value of the detection fields, the corrector circuit 76 subjects the detection signals to a necessary mathematical operation such as summing or averaging. The above-described field selecting process and this correction process are executed regardless of the regional type (see also to FIG. 10).

In the case where the regional type is the installation-priority type and it is determined by the AEC specifications that the source controller unit 11 includes an integrator circuit ("Yes" in step S18 of FIG. 14B), the detection signals from the corrector circuit 76 are transmitted as they are (as instantaneous values) at regular intervals from the detection signal interface 80 to the detection signal interface 26 of the source controller unit 11 (S19). In this case, merely the detection field selector circuit 75 and the corrector circuit 76 are actuated in the AEC section 67, as shown in FIG. 11.

On the other hand, in the case where the regional type is the installation-priority type but the source controller unit 11 does not includes any integrator circuit ("No" in step S18), the corrector circuit 76 outputs the detection signals to the integrator circuit 77 of the AEC section 67, so that the integrator circuit 77 integrates the detection signals (S20). Then the integrated value of the detection signals from the integrator circuit 77 is transmitted at regular intervals from the detection signal interface 80 to the detection signal interface 26 of the source controller unit 11 (S21). Transmission of the detection signals, either the instantaneous values or the integrated value, to the source controller unit 11 is repeated till the stop of x-ray radiation is detected ("Yes" in step S22). In this case, the detection field selector circuit 75, the corrector circuit 76 and the integrator circuit 77 are actuated in the AEC section 67, as shown in FIG. 12.

As described so far, where the regional type is the installation-priority type, instantaneous values or an integrated value of the detection signals is transmitted from the electronic cassette 13 to the source controller unit 11. Decision on the stop of x-ray radiation is made on the side of the source controller unit 11 using the transmitted instantaneous values or the integrated value of the detection signal. That is, the time to stop x-ray radiation is determined by comparing the integrated value of the detection signals with the stop-radiation threshold in the same way as conventional using the ex-AEC sensor 25. Consequently, where the installation-priority type is designated, the source controller unit 11 does not need any data on the stop-radiation threshold nor replacement of the threshold. The threshold replacement has to be done in the non-installation-priority type (see FIG. 10).

In a case where the regional type is the non-installation-priority type, all the components of the AEC section 67, including the comparator circuit 78 and the threshold circuit 79, are actuated, as shown in FIG. 13. Like the case where the regional type is the installation-priority type but the source controller unit 11 does not includes any integrator circuit, the corrector circuit 76 outputs the detection signals to the integrator circuit 77 of the AEC section 67, and the integrator circuit 77 integrates the detection signals (S23).

[Replacement of Threshold]

The threshold circuit 79 replaces the S values, which may be set as stop-radiation thresholds on the console 14, with such stop-radiation thresholds that are adjusted to the imaging conditions set in the source controller unit 11 (step S15 of FIG. 14A). As described so far, the source controller unit 11 allows assigning only one set of imaging conditions to one tube voltage (i.e. to one target site) and the same applies to the stop-radiation threshold, while multiple S values may be assigned to one tube voltage or target site on the console 14 (see FIG. 6). Accordingly, it is impossible to apply the multiple stop-radiation thresholds set as the S values directly to the source controller unit 11. For this reason, the threshold circuit 79 selects a representative S value from among the multiple sets of imaging conditions for the same tube voltage (i.e. for the same target site), and the threshold circuit 79 replaces the representative S value with a stop-radiation threshold which is assigned to the corresponding tube voltage in the source controller unit 11. For example, an S value preset for chest PA imaging is selected as the representative value in the console 14, and is replaced with a stop-radiation threshold which is predetermined for chest imaging in the source controller unit 11. If the corresponding stop-radiation threshold is modified in the source controller unit 11, the modified value is substituted for the representative S value. If the stop-radiation threshold is a default value in the source controller unit 11, the default value is substituted for the representative S value.

As for other S values, which are not representative but assigned to other styles of imaging of the same target site at the same tube voltage, the replacement of stop-radiation thresholds may be made through the following operations: converting the respective S values, including the representative S value, to radiation dose amounts; converting these radiation dose amounts to equivalent stop-radiation thresholds; calculating the ratio of each individual equivalent threshold to the other S value to an equivalent stop-radiation threshold to the representative S value, and multiplying the value of the stop-radiation threshold substituted for the representative S value by the calculated ratio. Thus, stop-radiation thresholds to be substituted for the other S values are determined.

For example, assuming that the image acquisition settings for chest PA imaging is selected as the representative imaging conditions at 120 kV tube voltage, that the stop-radiation threshold substituted for the S value for chest PA imaging is "6", that an original stop-radiation threshold equivalent to the S value for chest PA imaging is "5", and that an original stop-radiation threshold equivalent to an S value for chest AP imaging is "4", the stop-radiation threshold for chest AP imaging may be calculated by multiplying 6 by ⅘. Consequently, for chest AP imaging, the original stop-radiation threshold "4" equivalent to the S value is replaced with the stop-radiation threshold "4.8" in this example. Thus, the threshold circuit 79 supplies the comparator circuit 78 with those replacing stop-radiation thresholds which are adjusted to the imaging conditions set in the source controller unit 11, instead of the values set on the console 14.

The comparator circuit 78 compares the integrated value of the detection signals from the integrator circuit 77 with the stop-radiation threshold from the threshold circuit 79 (S24 in FIG. 14B), to output a radiation stopping signal ("Yes" in S25). The radiation stopping signal from the comparator circuit 78 is transmitted through the radiation signal interface 81 to the radiation signal interface 27 of the source controller unit 11 (S26).

Where the non-installation-priority type is designated as the regional type, the corrector circuit 76 converts the new AEC detection signals from the detective pixels 65 to such detection signals that correspond to the ex-AEC detection signals, and the converted detection signals are used for comparison with the substituted stop-radiation threshold that is adjusted to the imaging conditions in the source controller unit 11, in order to decide the time to stop x-ray radiation. Namely, the AEC section 67 of the electronic cassette 13 virtually executes the same procedure as the controller 21 of the source controller unit 11 executes using the ex-AEC sensor 25. However, since the stop-radiation threshold may vary depending on other imaging conditions set on the console 14 even for the same tube voltage, the AEC section 67 can control the exposure or radiation dose more finely than the source controller unit 11 do using the ex-AEC sensor 25.

As described so far, according to the present invention, the output address and the output format of electric signals for automatic exposure control are selected according to the regional type: the installation-priority type or the non-installation-priority type, flexible application of the radiography system 2 to the installation place will be achieved.

In the radiography system 2, stop-radiation thresholds set in the source controller unit 11 are kept unchanged, while the new AEC detection signals are corrected to be equivalent values to the ex-AEC detection signals before they are used for deciding the stop of radiation. Consequently, the electronic cassette 13 with the detective pixels 65 serving as the new AEC sensor may be combined with any type of x-ray source without the need for revising image acquisition settings on the source controller side. Generally, a radiography system may be constituted of an x-ray source and an x-ray image detector, which are made by different manufacturers from each other. In order to correct the stop-radiation thresholds preset in the source controller unit 11, it can take much time and labor calling a technician from the manufacturer of the x-ray source. To the contrast, in the radiography system 2 of the present invention, necessary corrections for the combination of the electronic cassette 13 with the x-ray source 10 are simply accomplished within the electronic cassette 13. This is certainly beneficial and promoting introduction of the new system using the new AEC signals. Moreover, according to the present invention, the new system may take over operators' intensions or guidelines of each hospital, which have previously been adopted in the existing system, e.g. dose reduction for less damage on the patient or dose enhancement for improved image resolution.

Furthermore, since the detection field selector circuit 75 selects the detective pixels 65 to provide the new AEC sensor with corresponding detection fields to those of the ex-AEC sensor 25, the automatic exposure control may be done in the same way as in the previous system.

It should be appreciated that the present invention is not limited to the above embodiment, but variously modified embodiments may be possible within the scope of the present invention.

Figure 15:
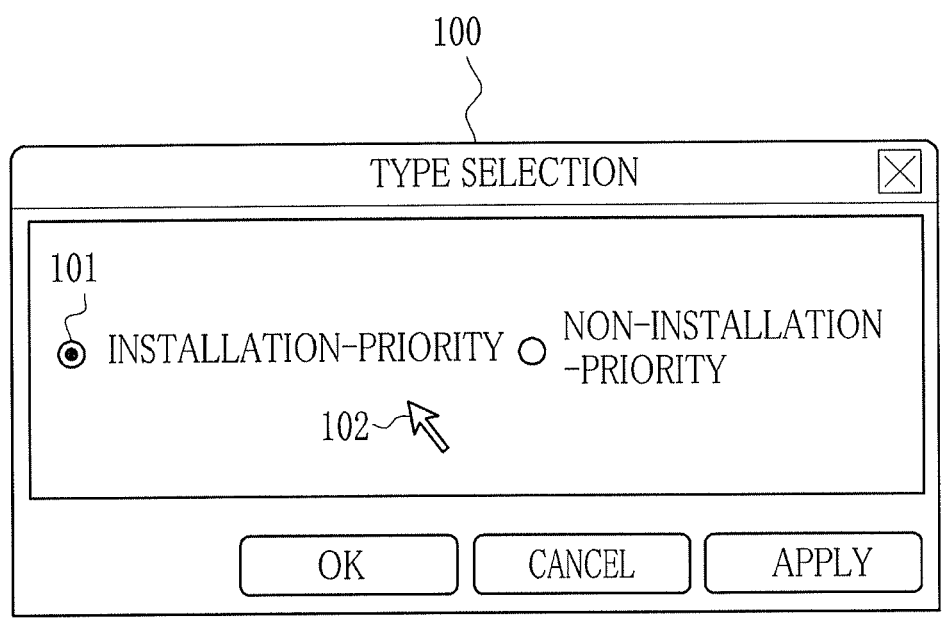
FIG. 15 is a diagram illustrating an example of a type selection window for manual input of the regional type.

In a modification, the regional type may be manually entered by the operator, while the above embodiment retrieves the regional type of the x-ray source 10 from the source data 99 using a source ID of the x-ray source 10 as a search key, which is received on the console 14 from the source controller unit 11 after the source controller unit 11 is installed and communicably connected to the console 14. In this modification, a selection window 100, like as shown in FIG. 15, may be displayed on the monitor 89 of the console 14 or on a not-shown display panel of the electronic cassette 13. The selection window 100 has a radio button 101 for alternative choice between the installation-priority type and the non-installation-priority type. The operator may choose either type by clicking a pointer 102 on the radio button 101 using the input device 90 or a not-shown operation member of the electronic cassette 13. Likewise, the source ID may be manually entered by the operator, instead of the automatic retrieval from the source data 99.

In another embodiment, the choice between the installation-priority type and the non-installation-priority type may be done at the shipment of the electronic cassette 13 or in an agent of the manufacturer by selecting one of two values preset in the electronic cassette 13. The electronic cassette 13 should be configured to switch its mode according to the selected type. Then it becomes unnecessary for the client such as a hospital to select the regional type when introducing the electronic cassette 13. Moreover, the manufacturer of the electronic cassette 13 is not required to prepare software for controlling the electronic cassette 13 specifically to the individual regional types or install such software in the cassette 13 according to the regional type. This will save time and cost of manufacture and increase the production efficiency of the electronic cassette 13.

[Use of Converter]

Figure 16:
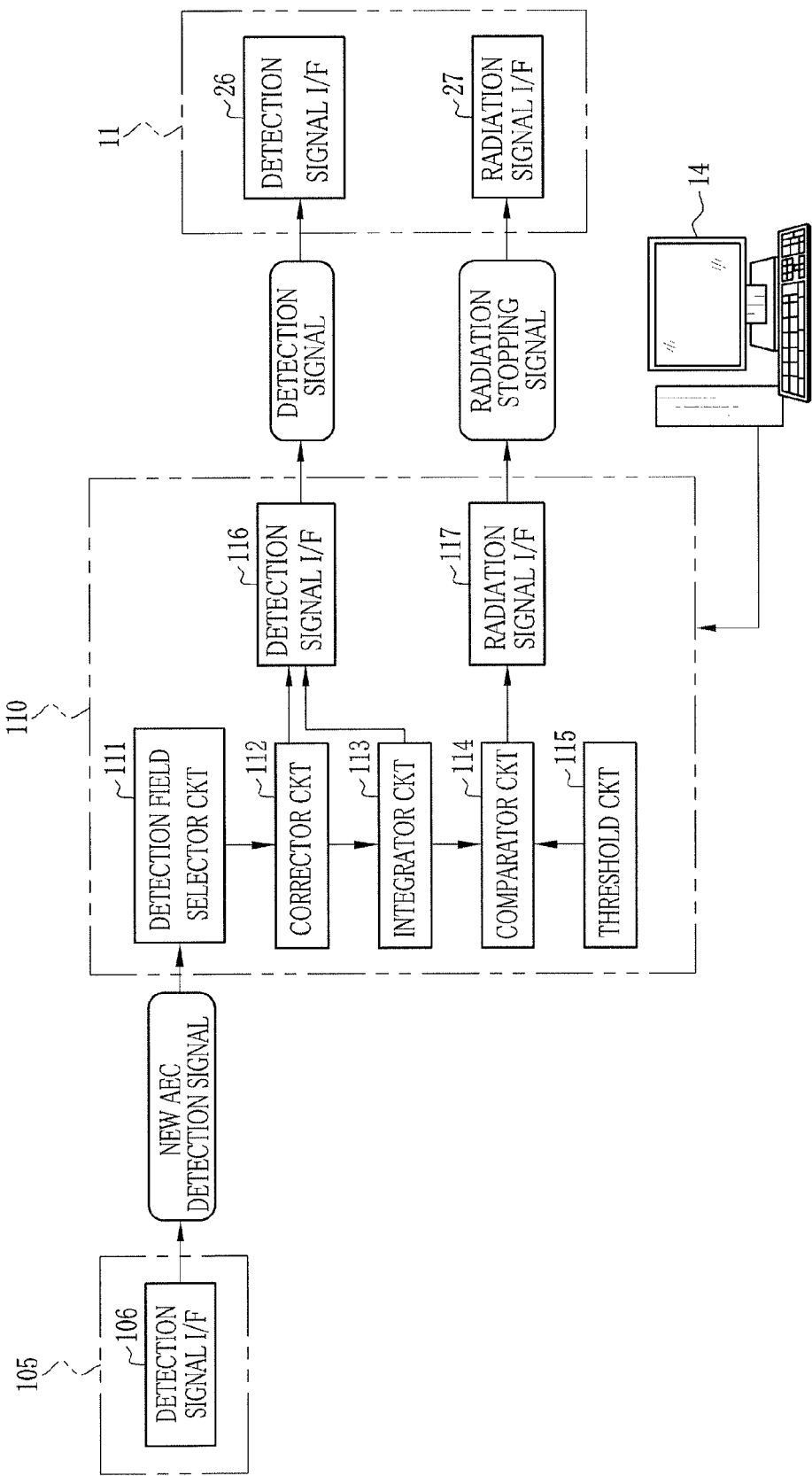
FIG. 16 is a block diagram illustrating an embodiment provided with a converter.

In the first embodiment, the electronic cassette 13 has both the detection signal interface 80 and the radiation signal interface 81, so that either of these interfaces is adoptable according to the regional type. In an alternative embodiment, as shown in FIG. 16, an electronic cassette 105 is only provided with a standard detection signal interface 106 which is configured to output the new AEC detection signals, but a converter 110 having the same functions as the AEC section 67 and the communicator section 40 of the electronic cassette 13 (see FIG. 5) is interconnected between the electronic cassette 105 and the source controller unit 11. The converter 110 may be used for selecting the output address and the output format of the detection signals.

In this embodiment, the converter 110 is connected to the console 14, to receive the source data 99, including the regional type, the AEC specifications, the correction data and the stop-radiation thresholds, from the console 14. The converter 110 includes a detection field selector circuit 111, a corrector circuit 112, an integrator circuit 113, a comparator circuit 114, a threshold circuit 115, a detection signal interface 116 and a radiation signal interface 117, all of which function in the same way as the detection field selector circuit 75, the corrector circuit 76, the integrator circuit 77, the comparator circuit 78 and the threshold circuit 79 of the AEC section 67, and the detection signal interface 80 and the radiation signal interface 81 of the communicator section 40, respectively. The converter 110 may decide the output address and the output format according to the regional type sent from the console 14, and maintains the same condition unless the x-ray source 10 is replaced with another.

Since the converter 110 takes over the functions of the AEC section 67 and the communicator section 40, the electronic cassette 105 may be reduced in size or weight as compared to the electronic cassette 13. Moreover, even if different regional types of x-ray sources are individually installed in multiple x-ray rooms of a hospital, because the electronic cassette 105 is connected to the source controller unit 11 via the converter 110, the electronic cassette 105 may be combined with any x-ray source without the need for switching the output format and output address of the detection signals on the cassette side, which would be necessary for the electronic cassette 13 of the first embodiment in that case.

[Convenience-Quality Balancing Type]

According to the first embodiment, where the regional type is the installation-priority type, the output address and the output format are set to be the detection signal interface and the voltage level (detection signal), respectively. In that case, the decision to stop x-ray radiation is made on the side of the source controller unit 11 using a threshold that is determined according to a limited number of available imaging conditions. Consequently, the image quality can be inferior to that acquired under more finely specified imaging conditions, i.e. on the basis of an optimized threshold available for fine exposure control on the side of the electronic cassette 13. An embodiment of FIG. 17 will achieve the fine automatic exposure control taking advantage of the new AEC system of the electronic cassette 13, while using the detection signal interface for the installation-priory type x-ray source.

In this embodiment, an AEC section 67 of an electronic cassette executes the same processes as in the case where the regional type is designated to be the non-installation-priority type in the first embodiment until the decision to stop radiation is made on the cassette side upon the integrated value of the detection signals from a correction circuit 76 reaches a stop-radiation threshold from a threshold circuit 79. However, the AEC section 67 does not use a radiation signal interface 81 but use a detection signal interface 80, and a comparator circuit 78 does not output a radiation stopping signal but outputs such a voltage signal from the detection signal interface 80 to the detection signal interface 26 of the source controller unit 11, that has an equal level to a stop-radiation threshold (e.g. th$1\alpha$) as preset for a current tube voltage (e.g. 120 kV) in the source controller unit 11.

As described above, the stop-radiation threshold generated from the threshold circuit 79 may have a different value even for the same tube voltage according to the image acquisition settings which are more-specifically designated on the console 14 (see FIG. 6), while only one or two values may be assigned as the stop-radiation thresholds to each tube voltage in the source controller unit 11. Accordingly, even at the same tube voltage, if the designated target site or other imaging condition is different, the AEC section 67 may make the decision on the stop of radiation at a variable time based on the different stop-radiation threshold generated from the threshold circuit 79. Therefore, in the embodiment of FIG. 17, the voltage signal having the equal level to the stop-radiation threshold preset for the current tube voltage in the source controller unit 11, which is sent from the electronic cassette 13 to the source controller unit 11, serves for a radiation stopping signal. In other words, the detection signal interfaces 26 and 80 function as interfaces for radiation stopping signal. Consequently, the decision on the time to stop radiation is actually made on the cassette side, but the source controller unit 11 virtually decides the stop of radiation upon receipt of the voltage signal of the same level as the stop-radiation threshold selected therein.

Figure 17:
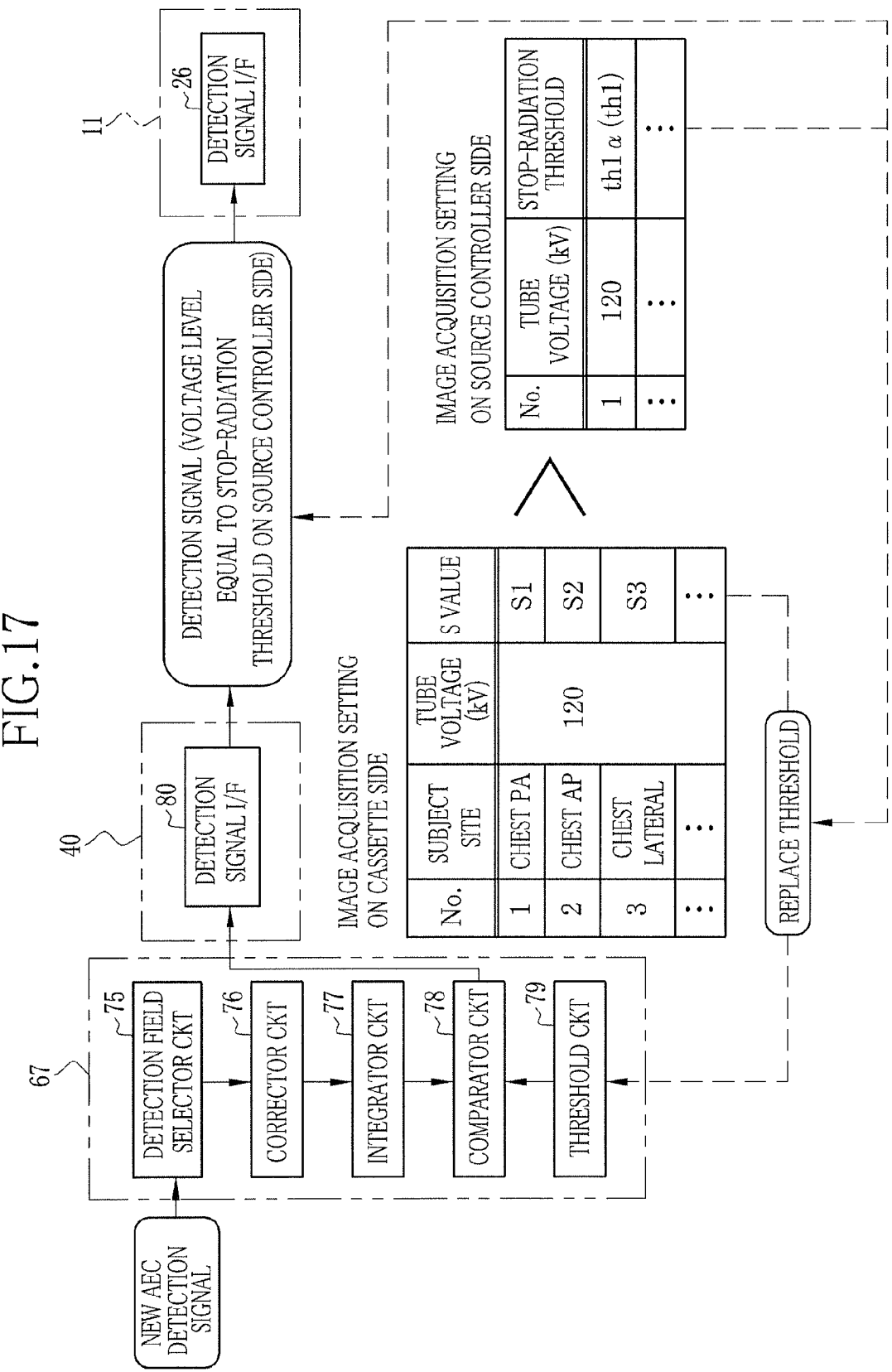
FIG. 17 is an explanatory diagram illustrating a method of adjusting thresholds available for the source controller unit to stop-radiation thresholds preset in the electronic cassette.

Thus, the embodiment of FIG. 17 makes good use of both the advantage of using the detection signal interface 80 for the sake of installation convenience and the advantage of using the radiation stopping signal from the electronic cassette 13 for the sake of image quality. This embodiment may be included as a convenience-quality balancing type in the regional types in addition to the installation-priority type and the non-installation-priority type of the above embodiment. There may be a case where more than one set of imaging conditions, i.e. more than one stop-radiation threshold, can be assigned to one tube voltage on the source controller side. In that case, a variety of sets of imaging conditions available for the AEC section 67 may be sorted into groups, and each group may be associated with one of the different sets of imaging conditions which are preset for the same tube voltage in the source controller unit 11. Then, a voltage signal having the same level as the stop-radiation threshold of the associated imaging conditions will be output as a radiation stopping signal to the source controller unit 11.

[Speeding AEC]

As described with respect to the above embodiment, the radiation signal interface 27 of the source controller unit 11 and the radiation signal interface 81 of the electronic cassette 13 exchange not only the radiation stopping signal but also other radiation signals such as the inquiry signal and the radiation admitting signal. Therefore, the radiation signal interfaces 27 and 81 have to sort the received signals and decide what kind of operation should be done in response to the individual signal. These processes take time. In addition, if the radiation signal interface 27 receives different signals at the same time, it may delay the required process for the automatic exposure control, especially the radiation stopping procedure. Since requisite exposure time for radiography is pretty short, e.g. the exposure time for chest imaging is 50 ms or so, the radiation stopping procedure should be done in no time.

Figure 18:
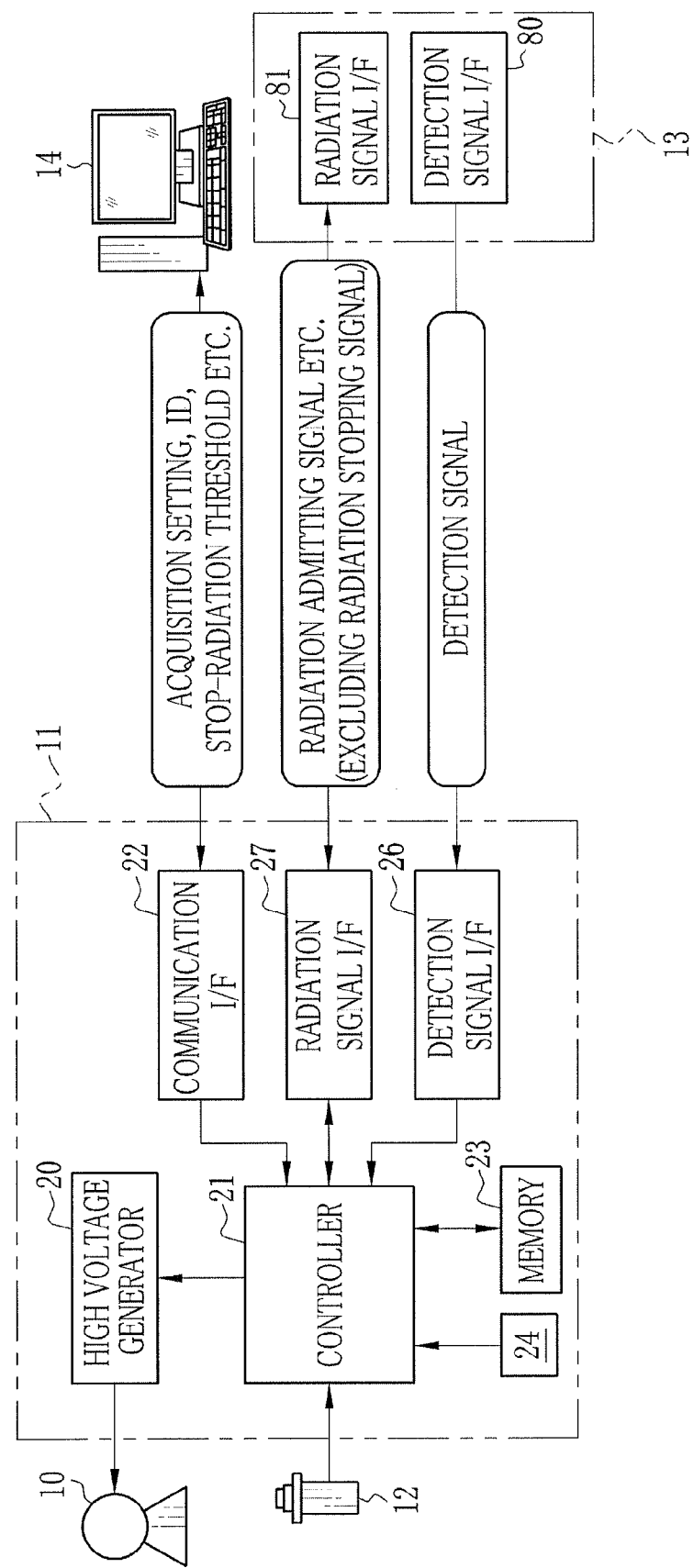
FIG. 18 is a block diagram illustrating an embodiment wherein radiation signals other than radiation stopping signal are exchanged through radiation signal interfaces, while detection signals are exchanged through detection signal interfaces.

For the sake of speeding the AEC operation, an embodiment shown in FIG. 18 is preferable, wherein both the detection signal interface 26 and the radiation signal interface 27 of the source controller unit 11 are connected to the detection signal interface 80 and the radiation signal interface 81 of the electronic cassette 13, respectively, so that the detection signal interfaces 26 and 80 exchange the detection signals, and the radiation signal interfaces 27 and 81 exchange other signals than the detection signal, except but the radiation stopping signal. Namely, the detection signals are processed and exchanged in the same way as for the installation-priority type in the first embodiment, whereas other signals, including the radiation admitting signal, are processed and exchanged in the same way as for the non-installation-priority type.

Alternatively, as shown in FIG. 19, a source controller unit 122 and an electronic cassette 123 may be provided with specific interfaces 120 and 121 for exchanging the radiation stopping signal only, in addition to and separately from the radiation signal interfaces 27 and 81. In this embodiment, the same process as for the non-installation-priority type in the first embodiment is executed, except that the radiation stopping signal is transmitted through the specific interfaces 120 and 121.

Transmitting the radiation stopping signal or the detection signal relevant to the decision on the stop of radiation through the specific interfaces separately from the interfaces for other signals will save the need for sorting the transmitted signals and deciding the required operations responsive to the respective signals. Moreover, these specific interfaces will not receive different kinds of signals at the same time. Consequently, the speed of the radiation stopping procedure will be improved.

Indeed it is possible to prevent other signals from being received simultaneously with the radiation stopping signal on the source controller side, by not transmitting the other signals simultaneously with the radiation stopping signal from the electronic cassette, but this method will complicate the signal transmission control process on the cassette side. To contrast, the embodiments of using specific interfaces for transmitting the radiation stopping signal or the detection signal relevant to the decision on the stop of radiation does not need any special transmission control therefor on the cassette side.

As described with respect to the prior art, a radiography system is often composed of an x-ray projector and an x-ray imaging apparatus of different markers from each other, and it is hard to specify how the signals exchanged between these machines would be processed inside the respective machines. For this reason, such an x-ray radiography system that includes an x-ray source and a source controller combined with an electronic cassette and a console of a different marker from that of the x-ray source and the source controller, it has been difficult to assure that the x-ray radiation stopping procedure will be done with no problem nor delay. On the contrary, according to the embodiments of FIGS. 18 and 19, using specific interfaces for transmitting the detection signal relevant to the decision on the stop of radiation or the radiation stopping signal, it is possible to assure the operation of the radiography system just by evaluating the performance of signal transmission from the electronic cassette and the performance of signal reception on the source controller unit, and confirming that the x-ray radiation stopping procedure is done with no problem nor delay.

As an alternative method for speeding the radiation stopping procedure, it may be possible to share the interfaces for the radiation stopping signal, which are used for the radiation stopping signal only in the embodiment of FIG. 19, with only those signals which will be transmitted at definitely different timing from the radiation stopping signal according to the processing sequence of the system. Because such signals will not interfere with the radiation stopping signal even if they are transmitted through the same interfaces, this configuration has substantially the same effect of speeding the radiation stopping procedure as the embodiment of FIG. 19. Specifically, for example the radiation start signal is not to be generated at the same time to stop the radiation, the radiation start signal may be transmitted through the same interfaces as for the radiation stopping signal. On the other hand, signals that can be generated at irregular timing, such as a battery level checking signal, should be transmitted through other interfaces. Note that this configuration is not applicable to the embodiment where the source controller decides the stop of radiation on the basis of the detection signals.

In the embodiments of FIGS. 18 and 19, the electronic cassette 13 or 123 may wirelessly communicate with the console 14, and the signal exchange between the radiation signal interface 27 of the source controller unit 11 or 122 and the radiation signal interface 81 of the electronic cassette 13 or 123 may also be done wirelessly. Adopting wired transmission to the detection signals or the radiation stopping signal is preferable in order to ensure the stability of the system. On the other hand, adopting wireless transmission to other signals will improve the maneuverability of the electronic cassette.

[Securing Safety]

If any of the detective pixels 65 of the electronic cassette 13 malfunctions or the communication between the source controller unit 11 and the electronic cassette 13 accidentally breaks during the imaging, transmission of the detection signal or the radiation stopping signal may not correctly be accomplished, resulting in failure of the automatic exposure control (AEC). Particularly, since a maximum value of the product of tube current and exposure time is preset as one imaging condition in the source controller unit 11, the radiation dose on the patient might go beyond an upper limit if the AEC would not work. To avoid the risk of overdose, it is preferable to provide the electronic cassette 13 with a test mode and execute test imaging in the test mode under individual sets of imaging conditions, for example, immediately after installation of the electronic cassette 13 or before executing actual imaging. In the test mode, the electronic cassette 13 continues detecting x-rays by the detective pixels 65 after it transmits the radiation stopping signal or the detection signal serving as the radiation stopping signal to the source controller unit 11, to check if the x-ray radiation stops within the determined time. If the answer is yes, it is judged that the AEC normally works. If not, it is judged that some trouble occurs in the system, and an alert is displayed on the monitor 89 of the console 14.

In the embodiment where the electronic cassette 13 and the source controller unit 11 are configured such that the detection signal interfaces 26 and 80 or the radiation signal interfaces 27 and 81 may be selectively connected wirelessly or in a wired fashion, it is preferable to monitor the condition of the wireless communication, such as radio field strength, and display an alert instructing to select the wired connection if the condition of the wireless communication is unstable.

The above embodiments have been described on the assumption that the radiography system 2 consists of one x-ray source 10, one electronic cassette 13 and one console 14, which are connected to each other in one-to-one relationship. This is merely for the illustrative purpose. In practice, the present invention is applicable to such a radiography system that is installed in a relatively large hospital having multiple x-ray rooms or boarded on round-visit cars, wherein one x-ray source and one console are disposed in each individual x-ray room or round-visit car, and more than one electronic cassette is selectively usable among the respective x-ray rooms or round-visit cars, or only one console supervises the operations of multiple x-ray sources.

In the former case, wherein the structure of the system in the individual x-ray room or round-visit car may be equal to any of the above embodiments, the x-ray source sends the source ID to the console upon the communication between this pair is established, like in the above embodiment. In the latter case, the operator may select one x-ray source for use in imaging from among the multiple x-ray sources, for example, by means of GUI on a monitor of the single console. The selected x-ray source transmits its source ID to the console.

In the above embodiment, the source data 99 of the x-ray source 10 is stored in the storage device 87 of the console 14, and the regional type and the correction data included in the source data 99 are sent from the console 14 to the electronic cassette 13. The present invention is not to be limited to this configuration, but the source data 99 may be stored in a not-shown internal memory of the controller 41 of the electronic cassette 13. In this alternative, the source ID should be transmitted to the electronic cassette via the console. In a radiography system including multiple x-ray sources, individual electronic cassettes may be provided with data on correlation between source IDs of the respective x-ray sources and ID data of console or, in the embodiment where the console and the electronic cassette are wirelessly connected, ID data of wireless access point, such as IP address, SSID or ESSID. Then the electronic cassette can obtain an ID of the console or the wireless access point as it is connected thereto, and retrieve a source ID that is correlated with the obtained console ID or the obtained access point ID from the correlation data. It is appreciated that the electronic cassette should obtain an ID from such a wireless access point that provides the best communicating condition, e.g. the highest radio field strength. In the case of a radiography system boarded on a round-visit car, an ID of the individual round-visit car may be used in place of the console ID or the wireless access point ID.

In the above embodiment, the new AEC sensor is constituted of the detective pixels 65 which are directly connected to the signal lines 52 without the interconnection of TFT 47, but the new AEC sensor may be configured otherwise. For example, making use of the fact that currents flowing through the bias lines 48 for applying the bias voltage Vb to every pixel 45 correspond to the electric charges generated in the pixels 45, the radiation dose may be detected by monitoring the current on one bias line that leads to one particular pixel 45. Alternatively, it is possible to detect the radiation dose on the basis of leak charges from the pixels 45 in a period while all TFTs 47 are OFF. It is also possible to provide at least a detective element having a different structure and an independent output from the pixels 45 on the same plane as the imaging area 36, specifically for the automatic exposure control.

While the detection signals are corrected before being integrated in the integrator circuit in the above embodiment, it is possible to correct the integrated value of the original detection signals instead. In this modification, the new AEC detection signals are fed from the detection field selector circuit to the integrator circuit, and the integrated value of the new AEC detection signals is corrected in the correction circuit in the same way as described with respect to the above embodiment.

In the above embodiment, the detective pixels 65 of the electronic cassette 13 are used as the AEC sensor in place of the ex-AEC sensor 25 that is attached to the x-ray source 10. The present invention is not only applicable to this retro-fitting, but also to other cases, e.g. where the electronic cassette is provided as an OEM (original equipment manufacturer) product of a manufacturer that produces the x-ray source and other components exclusive of the electronic cassette. Also in this case, it is necessary for the manufacturer of the electronic cassette to switch over the output format of signals for use in automatic exposure control such that these signals are compatible with the control system of the x-ray source and other components of the different manufacturer.

While the console 14 and the electronic cassette 13 have been described as separate units in the above embodiments, the console 14 is not necessarily an independent unit, but the function of the console 14 may be incorporated into the electronic cassette 13. Moreover, the present invention is applicable not only to portable x-ray image detectors like the electronic cassette, but also to stationary radiographic image detectors which are individually integrated into radiographic stands or tables.

Although the above embodiment is provided with the correction circuit 76 for correcting the new AEC detection signals to such detection signals that correspond to the ex-AEC detection signals in order to compensate for the inconsistency of AEC specifications between the source controller and the electronic cassette, the corrector circuit 76 is unnecessary if the compatibility between the source controller and the electronic cassette is established.

The present invention is applicable not only to x-ray radiography systems but also to radiography systems using other kinds of radioactive rays like gamma-rays.

The invention has been described in detail with particular reference to certain preferred embodiments thereof, but it will be understood that variations and modifications can be effected within the scope of the invention as described above, and as noted in the appended claims, by a person of ordinary skill in the art without departing from the scope of the invention.

What is claimed is:

1. A radiography system comprising:
   a radiation source for projecting radioactive rays toward a subject;
   a source controller unit for controlling activation of the radiation source; and
   a radiographic image detector for detecting a radiograph of the subject from radioactive rays penetrating the subject and being incident on an imaging plane of a detection panel, to output image data of the radiograph, wherein
   the radiographic image detector has a sensor for detecting the incident amount of radioactive rays and outputs exposure control signals to the source controller unit in order to stop radiation from the radiation source when an integrated amount of the radioactive rays reaches a predetermined threshold the radiographic image detector having the sensor on the detection panel, wherein
the source controller unit comprises:
a first signal interface for receiving directly from the radiographic image detector the exposure control signals only;
a second signal interface for receiving other signals than the exposure control signals, the other signals being outputted from the radiographic image detector; and
further comprising a console, provided separately from the source controller unit, for processing the radiograph detected by the radiographic image detector.

2. The radiography system as recited in claim 1, wherein the exposure control signals include detection signals from the sensor, an integrated value of the detection signals, or a radiation stopping signal that is generated based on the integrated value of the detection signals.

3. The radiography system as recited in claim 2, wherein the other signals include a radiation admitting signal.

4. The radiography system as recited in claim 1, wherein the radiographic image detector comprises a third signal interface for sending the exposure control signals only, and a fourth signal interface for sending the other signals.

5. The radiography system as recited in claim 4, wherein the fourth signal interface wirelessly transmits the other signals than the exposure control signals to the second signal interface.

6. The radiography system as recited in claim 1, wherein the radiographic image detector comprises a detection field selecting device for selecting a detection field of the sensor in accordance with a detection field of an ex-sensor which the source controller unit has previously used for automatic exposure control, on the basis of location data of the detection field of the ex-sensor when the sensor provided in the radiographic image detector is used in place of the ex-sensor.

7. The radiography system as recited in claim 6, wherein the detection field selecting device takes the posture of the radiographic image detector into consideration on selecting the detection field.

8. The radiography system as recited in claim 1, wherein the source controller unit transmits through the second signal interface an inquiry signal to the radiographic image detector inquiring whether the radiation source may start the radiation, and receives a radiation admitting signal from the radiographic image detector through the second signal interface.

9. The radiography system as recited in claim 1, wherein the sensor provided in the radiographic image detector comprises pixels which are directly connected to signal lines for reading out signal charges without any interconnected switching elements.

10. The radiography system as recited in claim 1, wherein the radiographic image detector is an electronic cassette that contains the detection panel in a portable housing.

11. A radiography system comprising:
a radiation source for projecting radioactive rays toward a subject;
a source controller unit for controlling activation of the radiation source; and
a radiographic image detector for detecting a radiograph of the subject from radioactive rays penetrating the subject and being incident on an imaging plane of a detection panel, wherein
the radiographic image detector has a sensor for detecting the incident amount of radioactive rays and outputs exposure control signals to the source controller unit in order to stop radiation from the radiation source when an integrated amount of the radioactive rays reaches a predetermined threshold, wherein
the source controller unit comprises:
a first signal interface for receiving the exposure control signals only; and
a second signal interface for receiving other signals than the exposure control signals, wherein the radiographic image detector comprises a correcting device for correcting detection signals from the sensor to be equivalent to detection signals from an ex-sensor which has been used by the source controller unit for automatic exposure control, when the sensor provided in the radiographic image detector is used in place of the ex-sensor in order to exclude influence of variations in intervening parts between the radiation source and the imaging plane of the detection panel of the radiographic image detector from the detection signals.

12. The radiography system as recited in claim 11, wherein the intervening parts include at least one of a housing that covers the detection panel of the radiographic image detector a scintillator for converting radioactive rays into visible light, and a grid for eliminating diffused radioactive rays as diffused through the subject.

13. The radiography system as recited in claim 11, wherein data of correlation between detection signals from the sensor and detection signals from the ex-sensor is stored in a storage device and the correcting device corrects detection signals from the sensor on the basis of the correlation data.

14. The radiography system as recited in claim 11, wherein the radiographic image detector comprises an integrating device for integrating the detection signals corrected through the correcting device.

15. The radiography system as recited in claim 14, wherein when the source controller unit has a function of integrating the detection signals, the radiographic image detector sends out the detection signals of the sensor as the exposure control signal, whereas when the source controller unit has no function of integrating the detection signals, the radiographic image detector sends out the integrated value of the detection signals as the exposure control signal.

16. The radiography system as recited in claim 14, wherein the radiographic image detector comprises a comparing device that compares the integrated value of the detection signals from the integrating device with a given threshold level and outputs a radiation stopping signal when the integrated value reaches the given threshold level.

17. A source controller unit for controlling activation of a radiation source to project radioactive rays toward a subject, the source controller unit comprising:
a first signal interface for receiving directly from a radiographic image detector only exposure control signals output from a sensor which detects the amount of radioactive rays having been projected toward and penetrated through the subject, the exposure control signal being used for stopping radiation from the radiation source when an integrated amount of the radioactive rays reaches a predetermined threshold; and
a second signal interface for receiving other signals than the exposure control signals, the other signals being outputted from the radiographic image detector, which includes the sensor on a detection panel and outputs image data of a radiograph.

18. The source controller unit as recited in claim 17, wherein the other signals include a radiation admitting signal.

* * * * *